United States Patent [19]
Manna et al.

[11] Patent Number: 6,036,667
[45] Date of Patent: *Mar. 14, 2000

[54] ULTRASONIC DISSECTION AND COAGULATION SYSTEM

[75] Inventors: Ronald Manna, Valley Stream; Scott Isola, Deer Park, both of N.Y.; H. Jonathan Tovey, Monroe; Dominick L. Mastri, Bridgeport, both of Conn.; Corbett W. Stone, San Diego, Calif.; Ernie Aranvi, Easton, Conn.

[73] Assignees: United States Surgical Corporation, Norwalk, Conn.; Misonix Incorporated, Farmingdale, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/911,207

[22] Filed: Aug. 14, 1997

Related U.S. Application Data

[60] Provisional application No. 60/027,599, Oct. 4, 1996.

[51] Int. Cl.⁷ .................................................. A61B 17/20
[52] U.S. Cl. ............................ 604/22; 606/170; 606/205
[58] Field of Search ............................ 604/22; 606/205, 606/207, 170, 171–180

[56] References Cited

U.S. PATENT DOCUMENTS

| | | |
|---|---|---|
| 2,002,594 | 5/1935 | Wappler et al. . |
| 2,011,169 | 8/1935 | Wappler . |
| 2,714,890 | 8/1955 | Vang . |
| 2,874,470 | 2/1959 | Richards . |
| 3,086,288 | 4/1963 | Balamuth et al. . |
| 3,427,480 | 2/1969 | Robinson . |
| 3,526,219 | 9/1970 | Balamuth . |
| 3,636,943 | 1/1972 | Balamuth . |
| 3,752,161 | 8/1973 | Bent . |
| 3,792,701 | 2/1974 | Kloz et al. . |
| 3,862,630 | 1/1975 | Balamuth . |
| 3,899,829 | 8/1975 | Storm et al. . |
| 3,930,173 | 12/1975 | Banko . |
| 4,428,748 | 1/1984 | Peyman et al. . |
| 4,672,965 | 6/1987 | Baum . |

(List continued on next page.)

FOREIGN PATENT DOCUMENTS

| | | |
|---|---|---|
| 0 394 583 | 10/1990 | European Pat. Off. . |
| 2 032 501 | 1/1972 | Germany . |
| 1 232 948 | 9/1989 | Japan . |
| 1-232949 | 9/1989 | Japan . |
| 63-061609 | 5/1993 | Japan . |
| 1155256 | 5/1985 | U.S.S.R. . |
| WO 86/02257 | 4/1986 | WIPO . |
| WO 94/20025 | 9/1994 | WIPO . |

OTHER PUBLICATIONS

International Search Report, dated Jan. 5, 1998.
U.S. Application Serial No. 08/925,184, Now Abandoned, filed Sep. 8, 1997.

Primary Examiner—John D. Yasko

[57] ABSTRACT

An ultrasonic dissection and coagulation system for surgical use is provided. The system includes an ultrasonic instrument, a control module, and a pedal actuator. The ultrasonic actuator has a housing and an elongated body portion extending from the housing. An ultrasonic transducer supported within the housing is operatively connected to a cutting blade by a vibration coupler. The vibration coupler conducts high frequency vibration from the ultrasonic transducer to the cutting blade. The cutting blade has a cutting surface which is angled with respect to the longitudinal axis of the elongated body portion and, thus, with respect to the axis of vibration. A clamp member having a tissue contact surface is positioned adjacent to the blade member and is movable from an open position in which the tissue contact surface is spaced form the cutting surface to a clamped position in which the tissue contact surface is in close juxtaposed alignment with the cutting surface to clamp tissue therebetween. The clamp member and the angled blade combine to enhance contact between tissue and the cutting surface of the blade member.

60 Claims, 33 Drawing Sheets

U.S. PATENT DOCUMENTS

| | | |
|---|---|---|
| 5,047,043 | 9/1991 | Kubota et al. . |
| 5,057,098 | 10/1991 | Zelman . |
| 5,059,210 | 10/1991 | Clark et al. . |
| 5,167,725 | 12/1992 | Clark et al. . |
| 5,180,363 | 1/1993 | Idemoto et al. . |
| 5,188,102 | 2/1993 | Idemoto et al. . |
| 5,190,541 | 3/1993 | Abele et al. . |
| 5,201,759 | 4/1993 | Ferzli . |
| 5,217,460 | 6/1993 | Knoepfler . |
| 5,222,937 | 6/1993 | Kagawa . |
| 5,263,957 | 11/1993 | Davison . |
| 5,267,998 | 12/1993 | Hagen . |
| 5,322,055 | 6/1994 | Davison et al. . |
| 5,334,183 | 8/1994 | Wuchinich . |
| 5,352,222 | 10/1994 | Rydell . |
| 5,389,104 | 2/1995 | Hahnen et al. . |
| 5,441,512 | 8/1995 | Muller . |
| 5,562,693 | 10/1996 | Devlin et al. . |
| 5,776,155 | 7/1998 | Beaupre et al. . |
| 5,800,448 | 9/1998 | Banko . |
| 5,810,559 | 9/1998 | DiMatteo et al. . |
| B1 5,322,055 | 10/1997 | Davison et al. . |

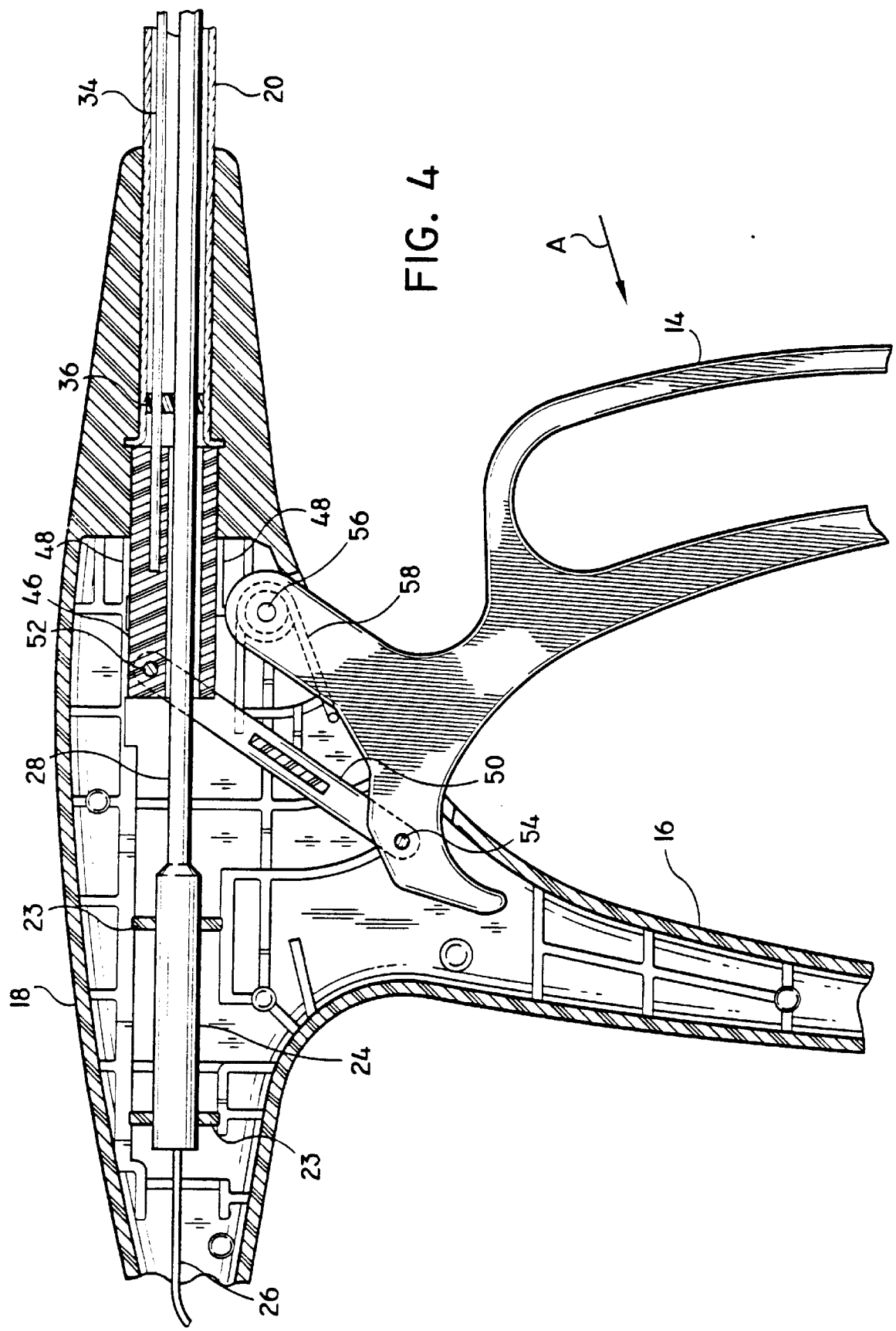

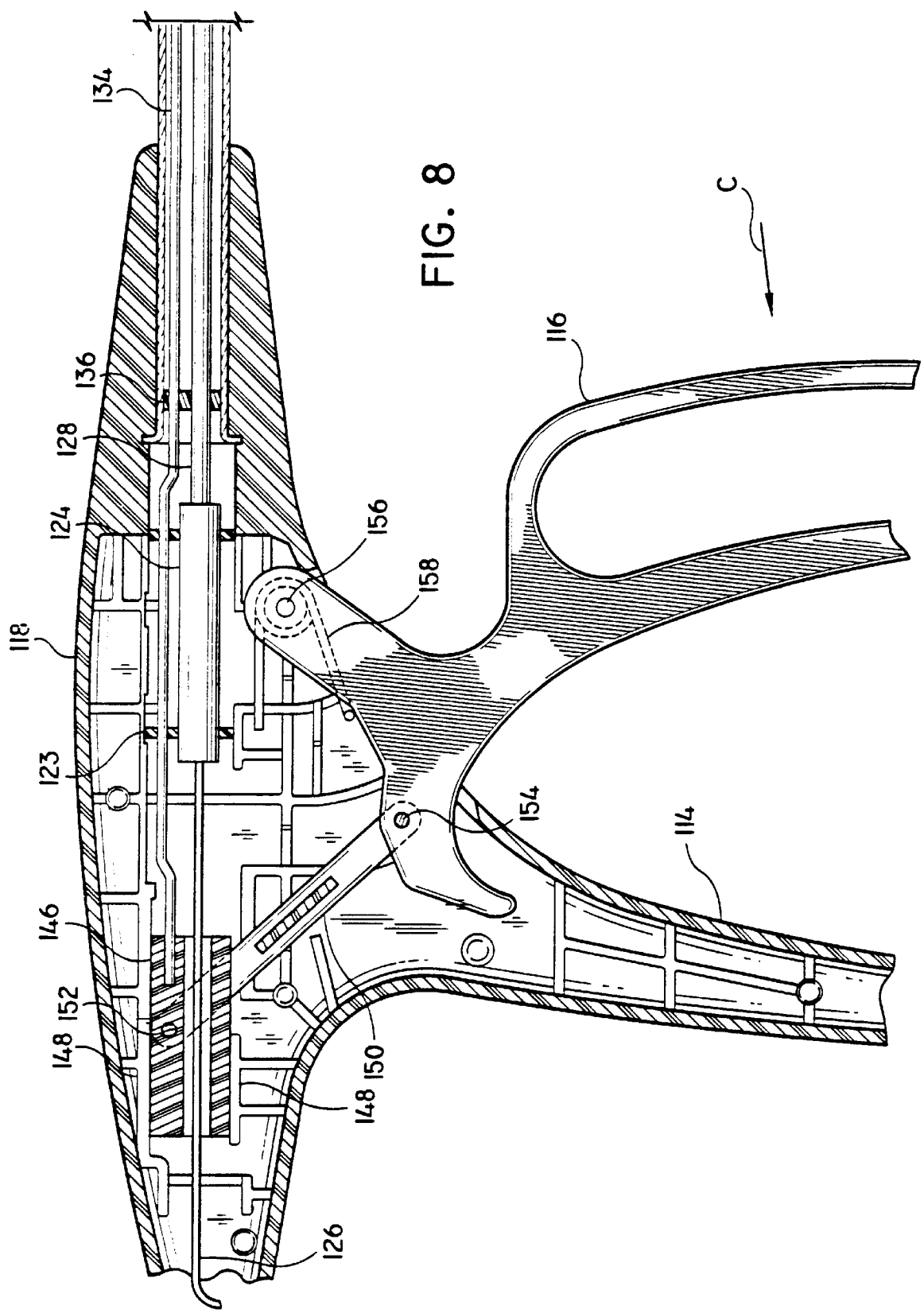

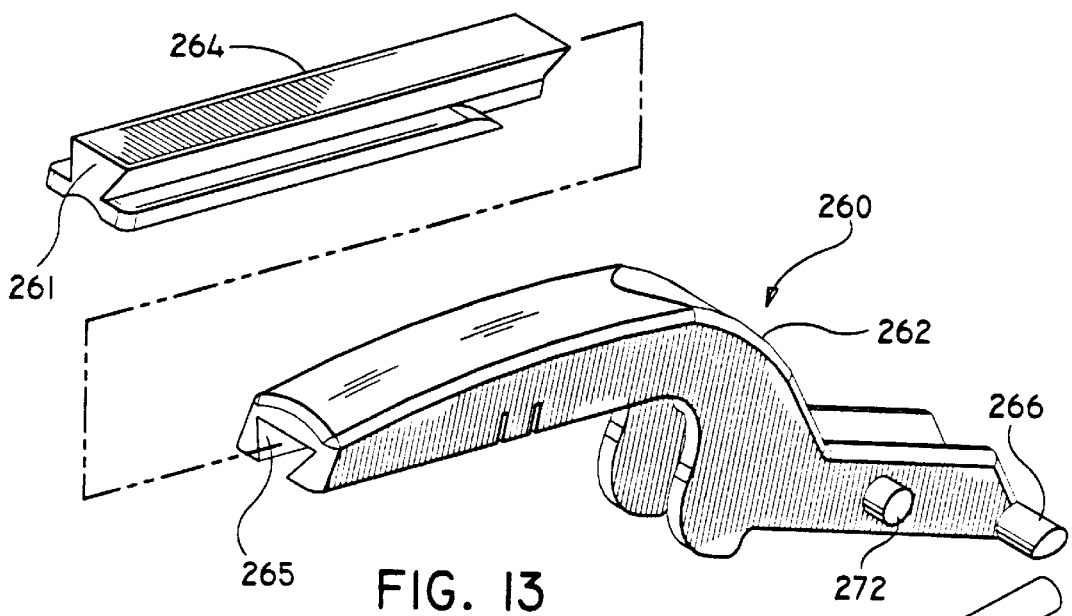
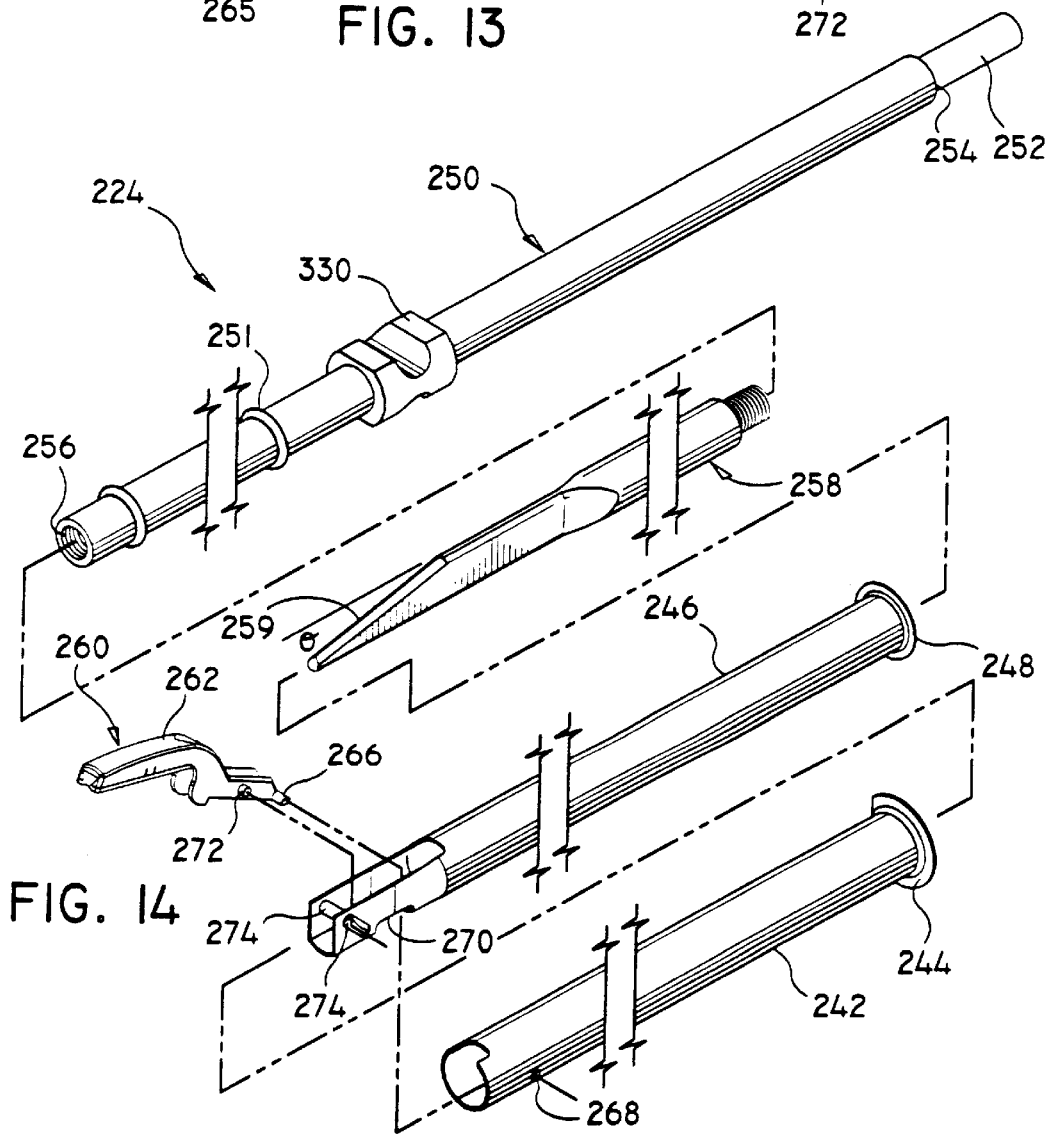

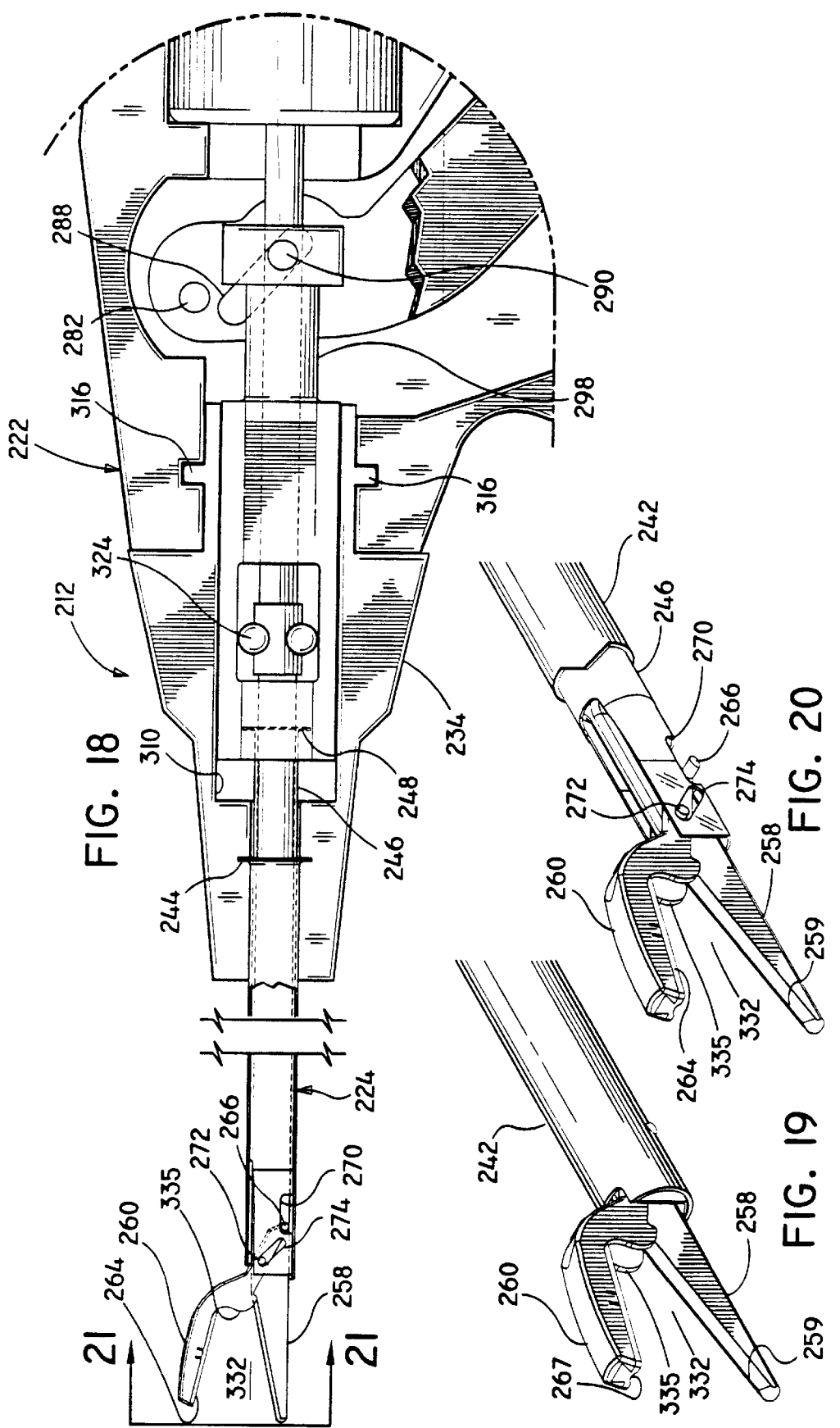

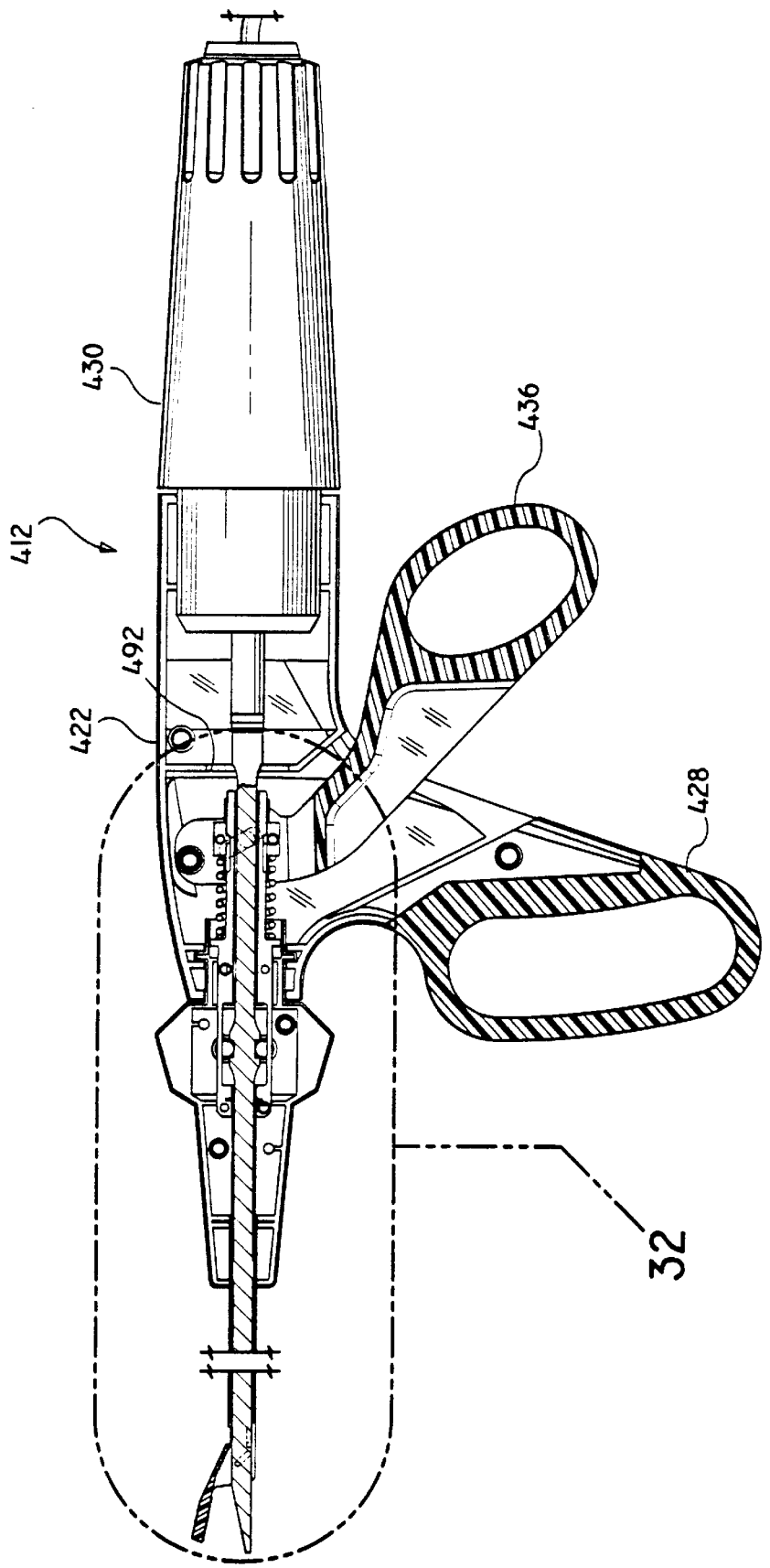

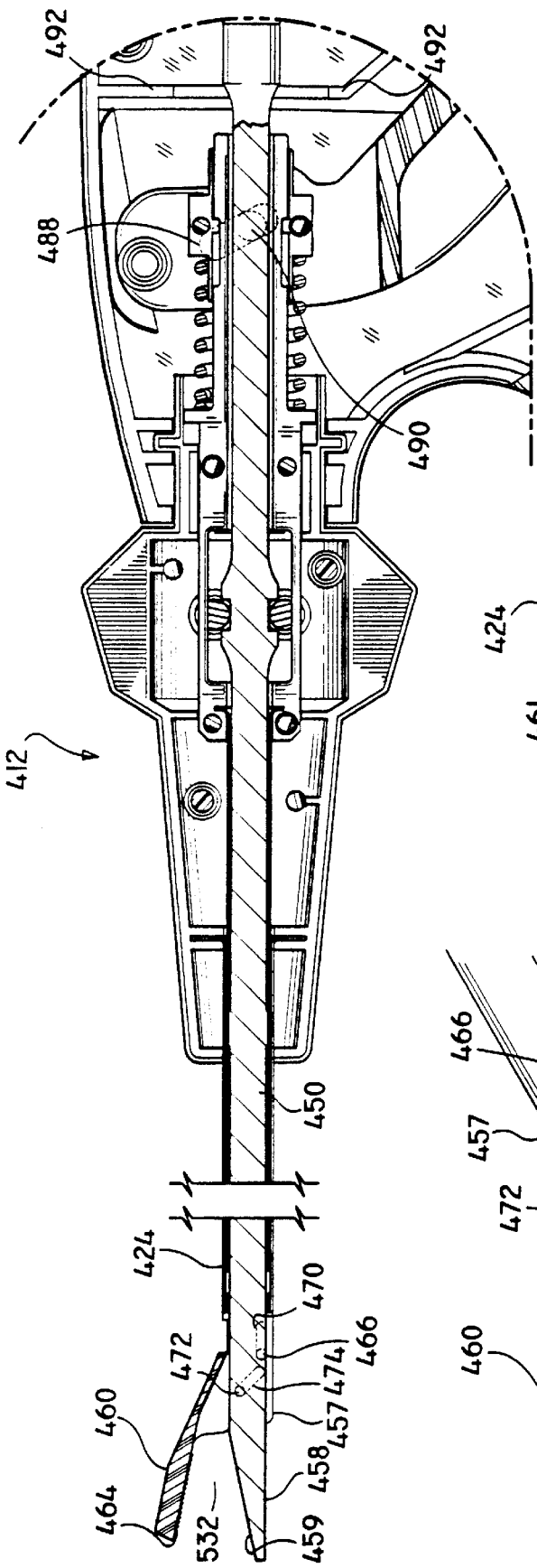
FIG. 32
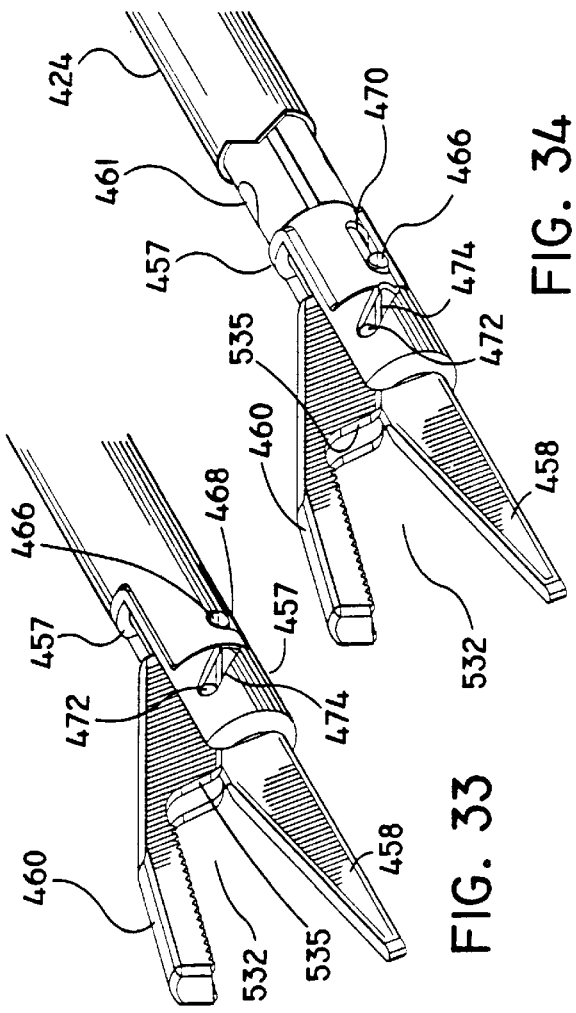
FIG. 33
FIG. 34

ULTRASONIC DISSECTION AND COAGULATION SYSTEM

This application claims benefit of Provisional Application Serial No. 60/027,599 filed Oct. 4, 1996.

BACKGROUND

1. Technical Field

The present disclosure relates to an ultrasonic dissection and coagulation system for surgical use. More specifically, the present disclosure relates to an ultrasonic instrument including an angled blade and a clamp member particularly suited for performing dissection and coagulation of tissue.

2. Background of Related Art

Ultrasonic instruments for surgical use and the benefits associated therewith are well known. For example, the use of an ultrasonic generator in conjunction with a surgical scalpel facilitates faster and easier cutting of organic tissue and accelerates blood vessel clotting in the area of the cut, i.e., accelerated coagulation. Improved cutting results from increased body tissue to scalpel contact caused by the high frequency of vibration of the scalpel blade with respect to body tissue. Improved coagulation results from heat generated by contact between the scalpel blade and the body tissue as the scalpel blade is vibrated at a high frequency. Thus, in order to reap the advantages associated with ultrasonic energy, good blade to tissue contact is important.

U.S. Pat. No. 3,862,630 ("Balamuth") discloses an ultrasonic system including an ultrasonic motor, a tool member having a working surface oriented normal to the direction of mechanical vibration generated by the ultrasonic motor, and a clamp member extending parallel to the tool member for compressing tissue against the tool member. U.S. Pat. No. 5,322,055 ("Davison") discloses an ultrasonic surgical instrument adapted for endoscopic use having a blade and a clamp movable in relation to the blade to capture tissue therebetween. The blade and the clamp define a clamping region having a plane which is parallel to the longitudinal axis of the surgical instrument. During an endoscopic procedure, movement of the instrument is limited to movement along an axis parallel to the plane of the clamping region. Thus, no additional blade force is imposed on the body tissue as a result of movement of the instrument.

Accordingly, a need exists for an improved ultrasonic surgical instrument which is easy to use and provides fast and easy cutting and improved coagulation.

SUMMARY

In accordance with the present disclosure, an ultrasonic tissue dissector is provided for dissection and coagulation of tissue. The surgical instrument includes a housing and a vibration coupler supported within the housing operably connected to an ultrasonic generator. An angled blade member is connected to the distal end of the vibration coupler to conduct high frequency vibration to the blade member. The blade member has a cutting surface that forms an obtuse angle with respect to an axis transverse to the longitudinal axis of the vibration coupler. The blade member may also have a width that tapers in the distal direction. A clamp member may be positioned adjacent to the blade member and is movable from an open position to a clamped position to capture tissue therebetween. The clamp member and angled blade member combine to enhance contact between the tissue and the blade member during operation of the instrument to improve the performance of the instrument.

In an alternate embodiment, the surgical instrument is operatively associated with a control module and a remote actuator and has a housing and an elongated body portion extending from the housing. An ultrasonic transducer supported within the housing is operatively connected to a cutting blade by a vibration coupler. The vibration coupler conducts high frequency vibration from the ultrasonic transducer to the cutting blade. The cutting blade has a cutting surface which is angled with respect to the longitudinal axis of the elongated body portion and, thus, with respect to the axis of vibration. A clamp member having a tissue contact surface is positioned adjacent to the blade member and is movable via an actuator tube from an open position in which the tissue contact surface is spaced from the cutting surface to a clamped position in which the tissue contact surface is in close juxtaposed alignment with the cutting surface to clamp tissue therebetween. Because the cutting blade is angled with respect to the longitudinal axis of the elongated body portion, the contact pressure applied by the blade surface is increased as the force applied to the instrument is increased.

BRIEF DESCRIPTION OF THE DRAWINGS

Various preferred embodiments are described herein with reference to the drawings, wherein:

FIG. 4 is a side cross-sectional view of the proximal end of the ultrasonic tissue dissector of FIG. 1;

FIG. 8 is a side cross-sectional view of the proximal end of the ultrasonic tissue dissector of FIG. 6 shown in the clamped position;

FIG. 13 is a perspective view with parts separated of the clamp of FIG. 11;

FIG. 14 is a perspective view with parts separated of the elongated body portion of the ultrasonic instrument of FIG. 11;

FIG. 19 is a perspective view of the distal end of the elongated body portion of the ultrasonic instrument of FIG. 11 with the clamp in the open position;

FIG. 20 is a perspective partial cutaway view of the distal end of the elongated body portion of the ultrasonic instrument of FIG. 11 with the clamp in the open position;

FIG. 31 is a side partial cross-sectional view of the ultrasonic instrument shown in FIG. 26 in the open position;

FIG. 32 is an enlarged view of the indicated area of detail of FIG. 31 illustrating the clamp in the open position;

FIG. 33 is a side perspective view of the distal end of the elongated body portion of the ultrasonic instrument shown in FIG. 33;

FIG. 34 is a side perspective, partial cutaway view of the distal end of the elongated body portion of the ultrasonic instrument shown in FIG. 33;

DETAILED DESCRIPTION OF THE PREFERRED EMBODIMENTS

Figure 1:
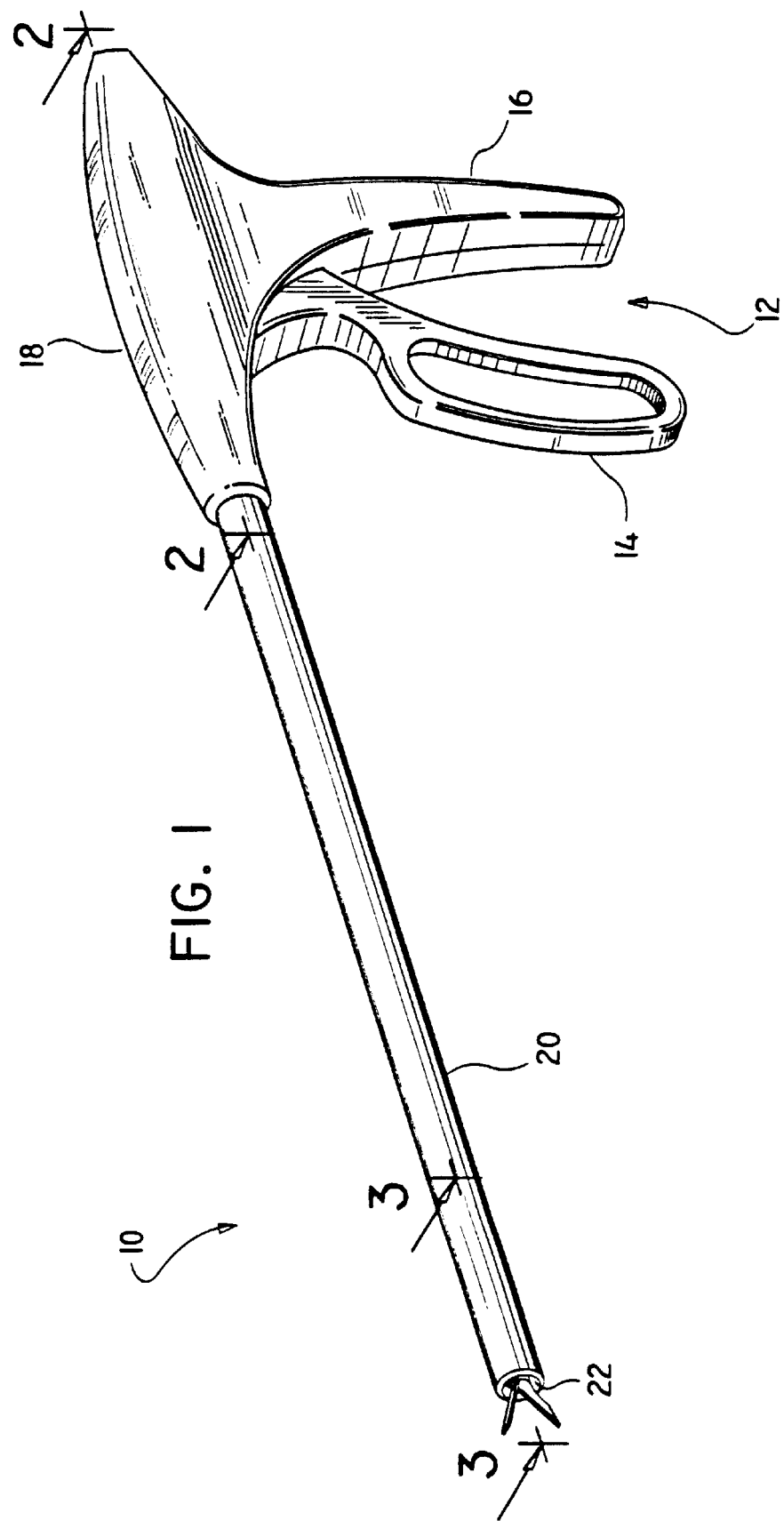
FIG. 1 is a perspective view of one embodiment of the ultrasonic tissue dissector in the open position.

Preferred embodiments of the presently disclosed ultrasonic dissection and coagulation system will now be described in detail with reference to the drawings, in which like reference numerals designate identical or corresponding elements in each of the several views.

FIGS. 1–5 illustrate one embodiment of the presently disclosed ultrasonic tissue dissector shown generally as 10 in FIG. 1. Briefly, ultrasonic tissue dissector 10 includes a handle assembly 12 including a movable handle member 14 and a stationary gripping member 16. A housing portion 18 is integrally formed with the stationary gripping member 16. Preferably, housing portion 18 and stationary gripping member 16 are monolithically constructed from two molded sections. A generally cylindrical elongated body portion 20 extends from the handle assembly 12 and is provided with an open distal end 22.

Figure 2:
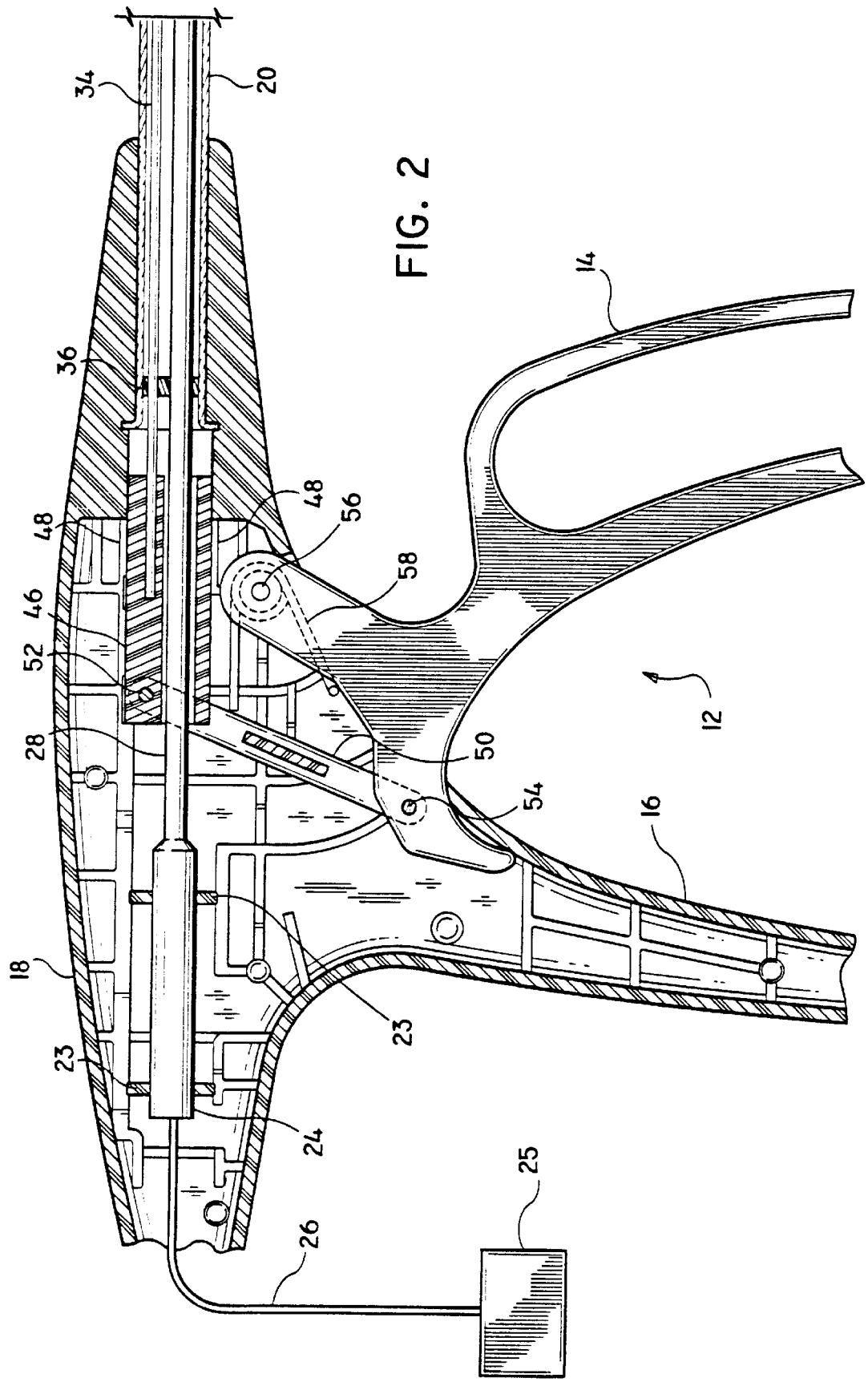
FIG. 2 is a side cross-sectional view taken along section line 2—2 of FIG. 1.
Figure 3:
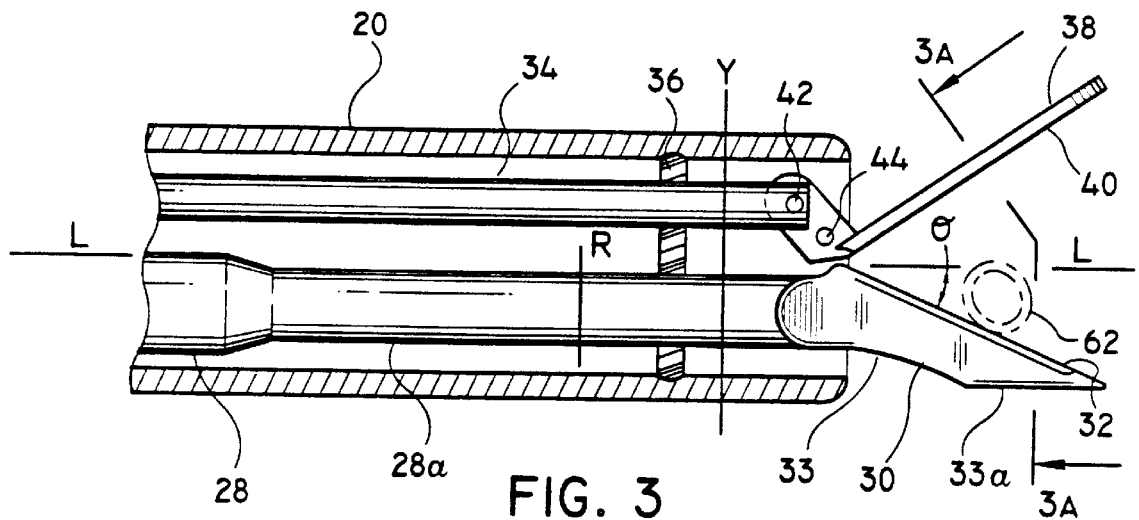
FIG. 3 is a side cross-sectional view taken along section line 3—3 of FIG. 1.

Referring to FIGS. 2–3, a transducer 24 is supported within housing portion 18 on support members 23 and is adapted to be connected to an ultrasonic generator 25 (shown schematically) via a power cable 26. A vibration coupler or horn 28 is positioned in engagement with transducer 24 and extends through elongated body portion 20. The vibration coupler 28 includes a tapered section 28a which is fixedly connected at its distal end to a blade member 30 having a cutting surface 32. The blade member 30 extends from open distal end 22 of elongated body portion 20. Alternately, the blade member 30 and the vibration coupler 28 may be integrally constructed. Blade member 30 has a straight cutting surface 32 angled away from the longitudinal axis of the coupler 28 (and elongated body portion 20) such that cutting surface 32 forms an obtuse angle with the transverse axis Y of the elongated body portion 20. Transverse axis Y is also parallel to the transverse axis R of the vibration coupler 28. As shown in the illustrated embodiment, the cutting surface 32 is angled downwardly and outwardly away from the central longitudinal axis of elongated body portion 20 and away from the clamp and actuation rod 34. Cutting surface 32 further defines a fixed acute angle Θ with respect to the longitudinal axis of the elongated body portion 20, which preferably ranges from about 15 degrees to about 70 degrees. A base portion 33 of blade 30 adjacent cutting surface 32 has a radius of curvature defining a smooth surface to prevent inadvertent damage to tissue or organs at a surgical site. The base portion 33 should not extend below the outer surface of elongated body portion 20 to facilitate passage through a cannula during an endoscopic procedure. Preferably, the base portion 33 extends outwardly to a position aligned with the outermost diameter of the vibration coupler 28.

Figure 3B:
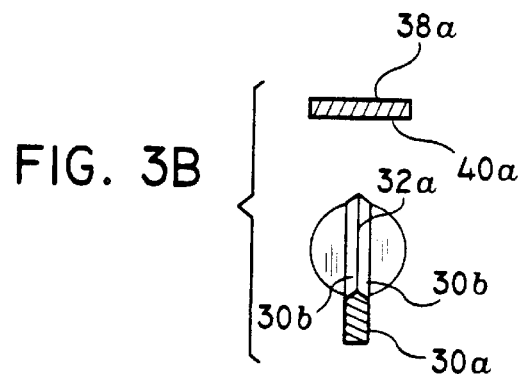
FIG. 3B is a cross-sectional view of the blade member and clamp of an alternate embodiment of the ultrasonic tissue dissector.
Figure 3A:
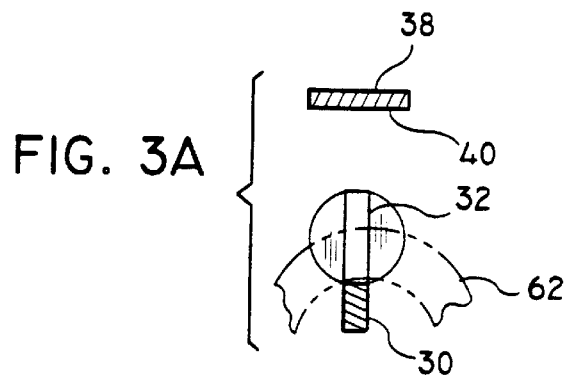
FIG. 3A is a front cross-sectional view taken along section line 3A—3A of FIG. 3.

FIG. 3A illustrates a cross-sectional view of the blade showing the blade having a generally planar cutting surface 32. FIG. 3B illustrates an alternate embodiment of the blade in which blade 30a has a top section having a triangular cross-section. Top walls 30b of blade 30a converge toward a linear edge which defines the cutting surface 32a. Alternately, a series of linear edges may be provided to define the cutting surface.

Referring to FIGS. 2 and 3, ultrasonic generator 25 supplies electrical energy having ultrasonic frequency to the transducer 24 to cause oscillation of the transducer 24 in a known manner. The transducer 24, which may be one of a variety of electromechanical types, e.g., electrodynamic, piezoelectric, magnetostrictive, is connected in end-to-end relation with the vibration coupler 28 to cause oscillation of the vibration coupler and corresponding oscillation of angled blade member 30.

An actuation rod 34 has a proximal end movably supported within housing portion 18. The actuation rod 34 extends through elongated body portion 20 and includes a distal end positioned adjacent the distal end of elongated body portion 20. Preferably, actuation rod 34 and vibration coupler 28 are supported within body portion 20 by support spacers 36, although any conventional support structure which allows for linear movement of the actuation rod may be used. Support spacers 36 are positioned at each end of vibration coupler 28 and actuation rod 34 adjacent a node on the vibration coupler 28. Additional spacers 36 can also be provided and positioned adjacent other nodes on the vibration coupler 28. A clamp 38 having a clamping surface 40 is connected to the distal end of the actuation rod 34 by a pivot pin 42. The clamp 38 also is pivotably connected to the distal end of elongated body portion 20 by a pivot pin 44 and is positioned adjacent to the blade 30 such that upon linear advancement of actuation rod 34, clamp surface 40 is moved into juxtaposed alignment with cutting surface 32. Due to the angle of the clamp surface 40 and cutting surface 32, tissue is pulled proximally towards the cutting surface 32 when clamped.

The proximal end of the actuation rod 34 is frictionally received in a slidable coupling 46 positioned within the housing portion 18. Coupling 46 is restricted to linear movement by walls 48 of housing portion 18. Movable handle 14 is operably connected to coupling 46 by link 50 which is pivotably connected at one end to coupling 46 by pin 52 and pivotably connected at its opposite end to movable handle 14 by pin 54. Movable handle 14 is pivotably connected to housing portion 18 by pivot pin 56. A biasing member 58 is positioned within the housing to bias movable handle 14 distally (counterclockwise) to thereby maintain coupling 46 proximally within housing portion 18 and maintain actuation rod 34 in a retracted position. When actuation rod 34 is in the retracted position, clamp 38 is in an open position (see FIG. 3). Alternately, the clamp 38 can be biased to a clamping (closed) position.

In use, ultrasonic tissue dissector 10 is grasped about the handle assembly 12 and moved to position the cutting surface 32 adjacent tissue 62 to be dissected and/or coagulated (See FIG. 3A). Because the movable handle 14 in the illustrated embodiment is biased by biasing member 58 to the open position, ultrasonic tissue dissector 10 can be positioned without operation of movable handle 14.

Figure 5:
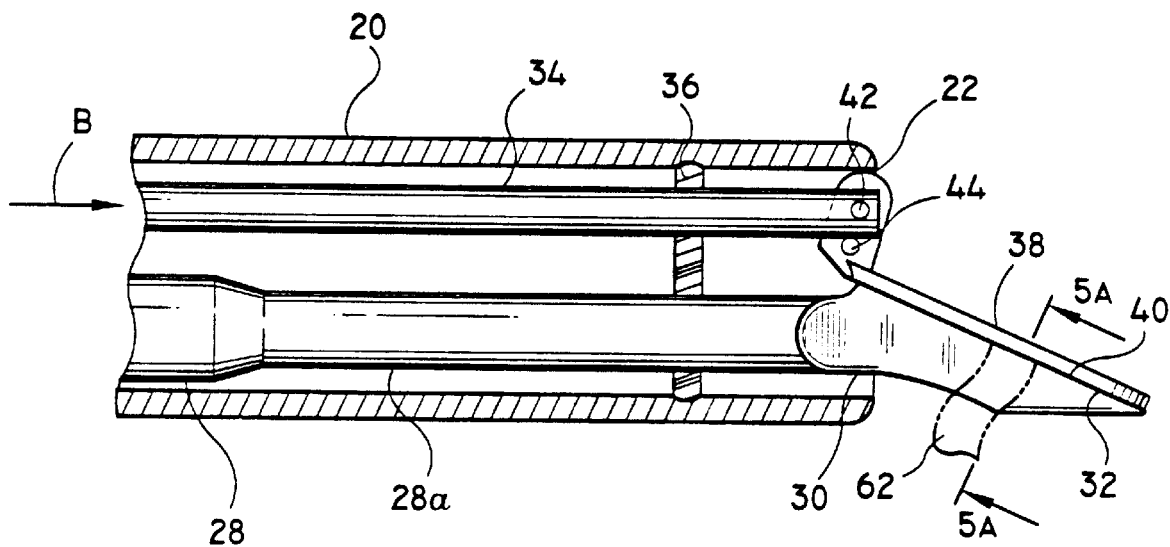
FIG. 5 is a side cross-sectional view of the distal end of the ultrasonic tissue dissector of FIG. 1 shown in the clamped position.
Figure 5A:
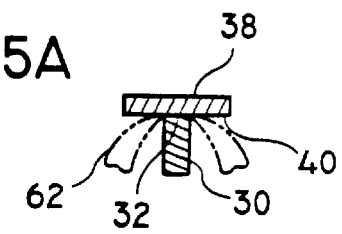
FIG. 5A is a cross-sectional view taken along section line 5A—5A of FIG. 5.

Referring now to FIGS. 4 and 5, after ultrasonic tissue dissector 10 is properly positioned about body tissue 62, movable handle 14 is pivoted in a clockwise direction, as indicated by arrow "A" in FIG. 4, to advance slidable coupling 46 distally, via link 50. Movement of coupling 46 advances actuation rod 34 distally, as indicated by arrow "B" in FIG. 5, to pivot clamp 38 clockwise about pivot pin 44 and clamp tissue 62 between cutting surface 32 and clamping surface 40. See FIG. 5A. The ultrasonic generator may now be energized to cause linear oscillation of blade 30 with respect to clamp 38 to effect dissection and/or coagulation of tissue 62.

Figure 6:
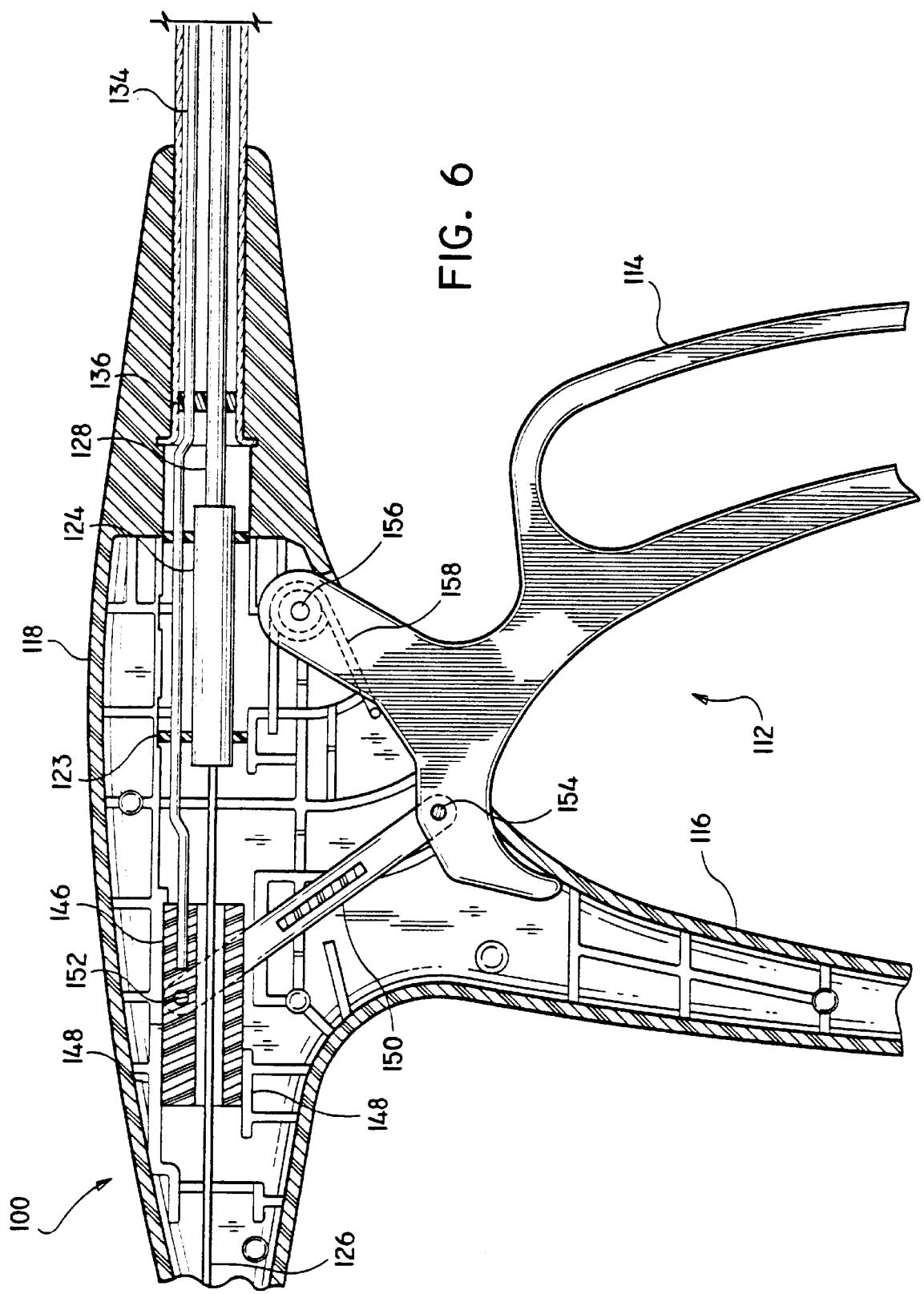
FIG. 6 is a side cross-sectional view of the proximal end of an alternate embodiment of the ultrasonic tissue dissector shown in the open position.
Figure 7:
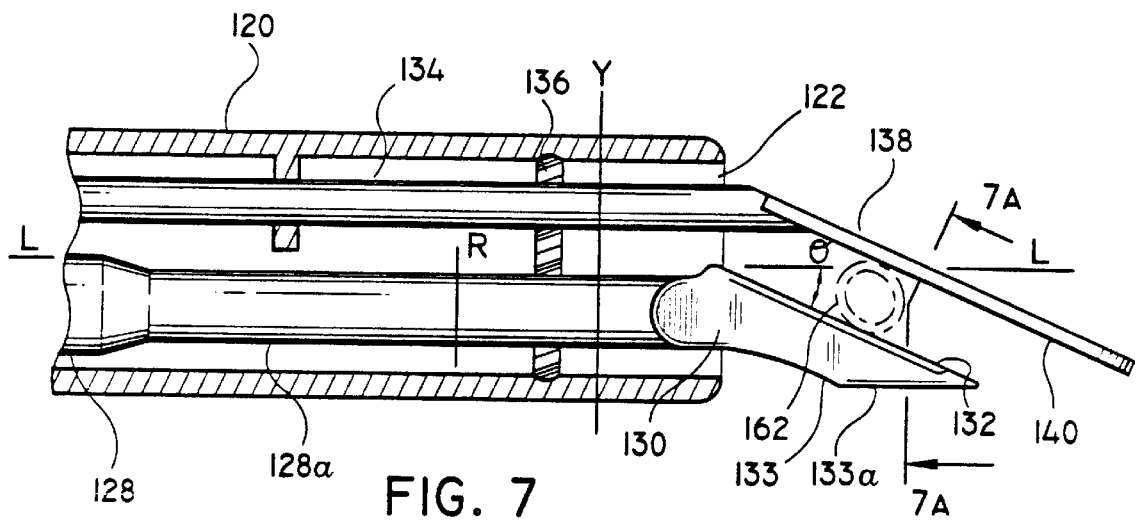
FIG. 7 is a partial side cross-sectional view of the distal end of the ultrasonic tissue dissector of FIG. 6 shown in the open position.

FIGS. 6–9 illustrate an alternate embodiment of the presently disclosed ultrasonic tissue dissector shown generally in FIG. 6 as 100. Referring to FIGS. 6 and 7, ultrasonic tissue dissector 100 includes a handle assembly 112 including a movable handle 114 and stationary gripping member 116. A housing portion 118 is integrally formed with the stationary gripping member 116. Preferably, housing portion 118 and stationary gripping member 116 are monolithically constructed from two molded sections. A generally cylindrical elongated body portion 120 extends from the handle assembly 112 and is provided with an open distal end 122.

As illustrated in FIGS. 6 and 7, a transducer 124 is supported within housing 118 on support members 123 and is adapted to be connected to an ultrasonic generator (not shown) via a power cable 126. Vibration coupler 128 is positioned in engagement with transducer 124 and extends through elongated body portion 120. The vibration coupler 128 includes a tapered section 128a which is fixedly connected at its distal end to a blade member 130 having a cutting surface 132. Blade member 130 extends from open distal end 122 of elongated body portion 120. Alternately, blade member 130 and vibration coupler 128 may be integrally constructed. Blade member 130 has a generally straight cutting surface 132 which is angled away from the longitudinal axis of the coupler 128 and elongated body portion 120 such that cutting surface 132 forms an obtuse angle with respect to a transverse axis Y of the elongated body portion 120. Transverse axis Y is also parallel to the transverse axis R of the vibration coupler 28. As shown in the illustrated embodiment, the cutting surface 132 is angled downwardly and outwardly away from the central longitudinal axis of elongated body portion 120 and away from the clamp and clamp actuation rod 134. Cutting surface 132 defines a fixed acute angle Θ, with respect to the longitudinal axis of elongated body portion 120 preferably, from about 15 degrees to about 70 degrees. A base portion 133 of blade 130 adjacent cutting surface 132 has a radius of curvature defining a smooth surface which prevents inadvertent damage to tissue or organs at a surgical site. Base portion 133 should not extend below the outer surface of elongated body portion 120 to facilitate passage through a cannula during an endoscopic procedure. Preferably, base portion 133 extends outwardly a distance aligned with the outermost diameter of the vibration coupler 128.

Figure 7A:
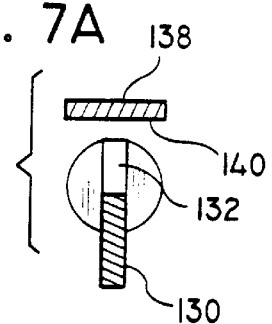
FIG. 7A is a cross-sectional view taken along section line 7A—7A of FIG. 7.
Figure 7B:
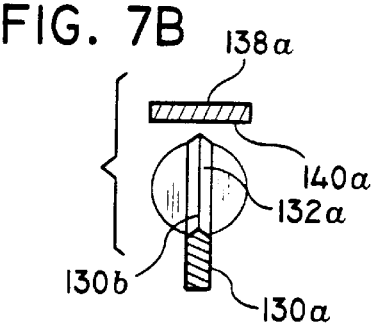
FIG. 7B is a cross-sectional view of the blade member and clamp of an alternate embodiment of the ultrasonic tissue dissector.

FIG. 7A illustrates a cross-sectional view of the blade showing the blade having a generally planar cutting surface 132. FIG. 7B illustrates an alternate embodiment of the blade in which the blade 130a has a top section having a triangular cross-section. Top walls 130b of the blade 130a converge toward a linear edge which defines the cutting surface 132a. Alternately, a series of linear edges may be provided to define the cutting surface.

Figure 7C:
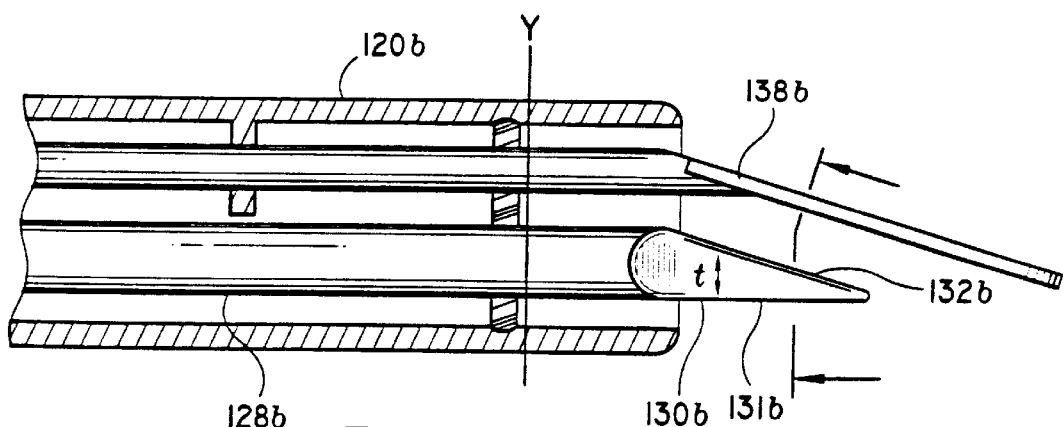
FIG. 7C is a cross-sectional view of the distal end of another alternate embodiment of the ultrasonic tissue dissector.

FIG. 7C illustrates a side cross-sectional view of another alternate embodiment of the blade. Blade 130b has a first surface 131b parallel to the longitudinal axis of the vibration coupler 128b (and body portion 120b). A straight cutting surface 132b is angled away from the longitudinal axis of the coupler 128b (and elongated body portion 120b) such that cutting surface 132b forms an obtuse angle with the transverse axis Y of the elongated body portion 120. Blade 130b tapers in thickness toward its distal end. Although shown in conjunction with linearly movable clamp 138b, blade 130b, alternatively, may be used in conjunction with a pivotable clamp.

Referring again to FIGS. 6 and 7, an actuation rod 134 has a proximal end movably supported within housing portion 118. The actuation rod 134 extends through elongated body portion 120 and includes a distal end positioned adjacent the distal end of elongated body portion 120. Preferably, actuation rod 134 and vibration coupler 128 are supported within body portion 120 by support spacers 136, although any conventional support structure which allows for linear movement of the actuation rod may be used. Support spacers 136 are positioned at each end of the vibration coupler 128 and actuation rod 134 adjacent a node on the vibration coupler 128. Additional spacers can also be provided and positioned adjacent other nodes. A clamp 138 is connected to the distal end of the actuation rod 134 and includes clamp surface 140 which is parallel to and faces cutting edge 132 of blade member 130. The clamp 138 is movable with respect to the blade member 130 from an open position to a clamped position to capture tissue between the cutting edge 132 and the clamp surface 140. In the clamped position, cutting edge 132 and clamp surface 140 are in juxtaposed alignment. Alternately, clamp 138 may be formed integrally with the actuation rod 134 and may have a smooth texture, although a knurled or ribbed surface may be provided to facilitate grasping of tissue or to enhance coagulation. Due to the angle of the clamp surface 140 and cutting surface 132, tissue is pulled proximally towards the cutting surface 132 when clamped.

The proximal end of the actuation rod 134 is frictionally received in a slidable coupling 146 positioned within the housing portion 118. The coupling 146 is restricted to linear movement by walls 148 of housing portion 118. Movable handle 114 is operably connected to slidable coupling 146 by a link 150 which is pivotably connected at one end to the coupling 146 by pin 152 and pivotably connected at its opposite end to movable handle 114 by pin 154. Movable handle 114 is pivotably connected to housing portion 118 by pivot pin 156. A biasing member 158 is positioned within housing portion 118 to bias the movable handle 114 distally to thereby maintain coupling 146 distally within housing portion 118 and maintain actuation rod 134 in a distal position. When actuation rod 134 is in its distal position, clamping surface 140 is spaced from cutting surface 132 to define the open position of the ultrasonic tissue dissector 100. Alternately, the clamp member can be biased to an open position.

In use, ultrasonic tissue dissector 100 is grasped about the handle assembly 112 and moved to position the cutting surface 132 adjacent body tissue 162 to be dissected and/or coagulated (See FIGS. 7 and 7A). Because the movable handle in the illustrated embodiment is biased by biasing member 158 to the open position, the clamp is in the distal position and ultrasonic tissue dissector 100 can be positioned about tissue without operation of movable handle 14.

Figure 9:
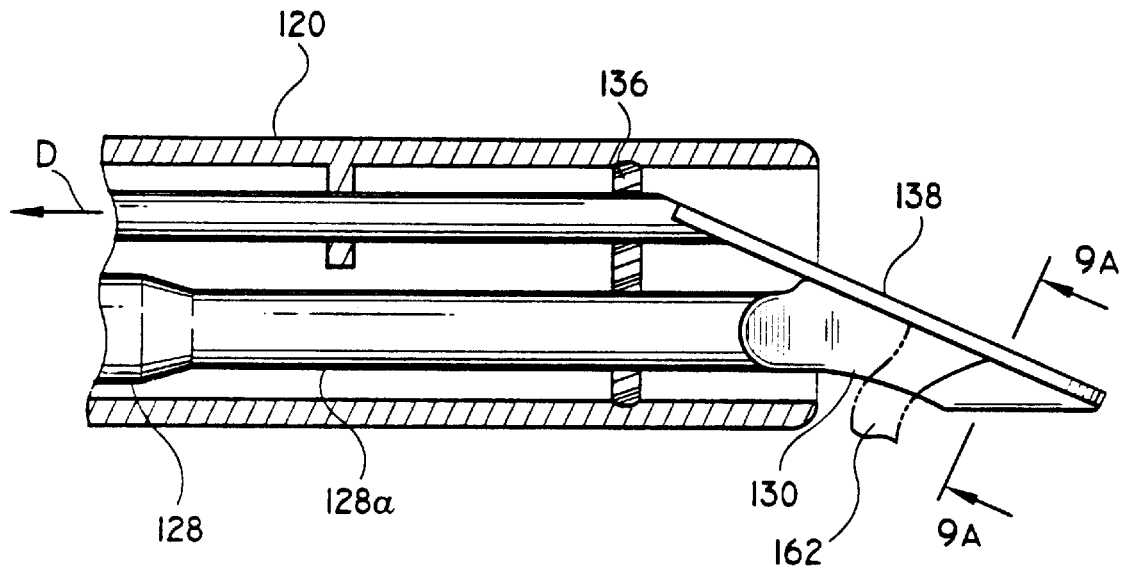
FIG. 9 is a cross-sectional view of the distal end of the ultrasonic tissue dissector of FIG. 6 shown in the clamped position.
Figure 9A:
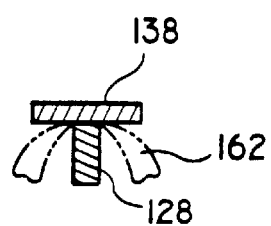
FIG. 9A is a cross-sectional view taken along section line 9A—9A of FIG. 9.

Referring now to FIGS. 8 and 9, after ultrasonic tissue dissector 100 is properly positioned about body tissue 162, movable handle 114 is pivoted in a clockwise direction, as indicated by arrow "C" in FIG. 8 to move slidable coupling 146, via link 150, proximally within housing portion 118. Movement of coupling 146 moves actuation rod 134 proximally as indicated by arrow "D" in FIG. 9 to move clamping surface 140 into alignment with cutting surface 132 to clamp tissue 162 therebetween. The ultrasonic generator may now be energized to cause linear oscillation of blade 130 with respect to clamp 138 to effect dissection and/or coagulation of tissue 162.

Figure 10:
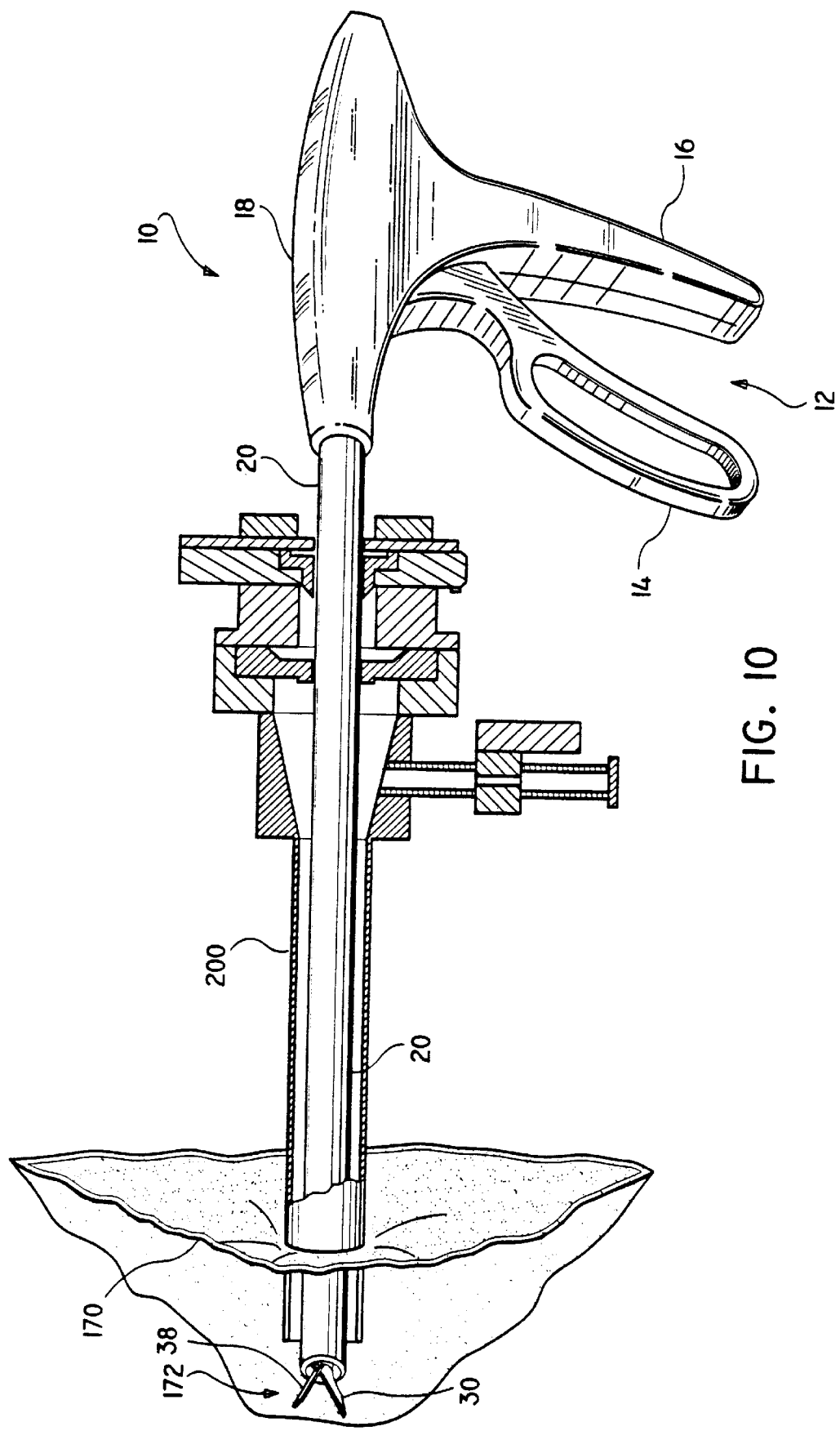
FIG. 10 is a partial cross-sectional view showing the ultrasonic tissue dissector positioned in a trocar cannula.

FIG. 10 illustrates endoscopic use of the ultrasonic tissue dissector. As shown, ultrasonic tissue dissector 10 (or alternately dissector 100) is inserted through body tissue 170 via cannula 198 into cavity 172 to access tissue.

Figure 11:
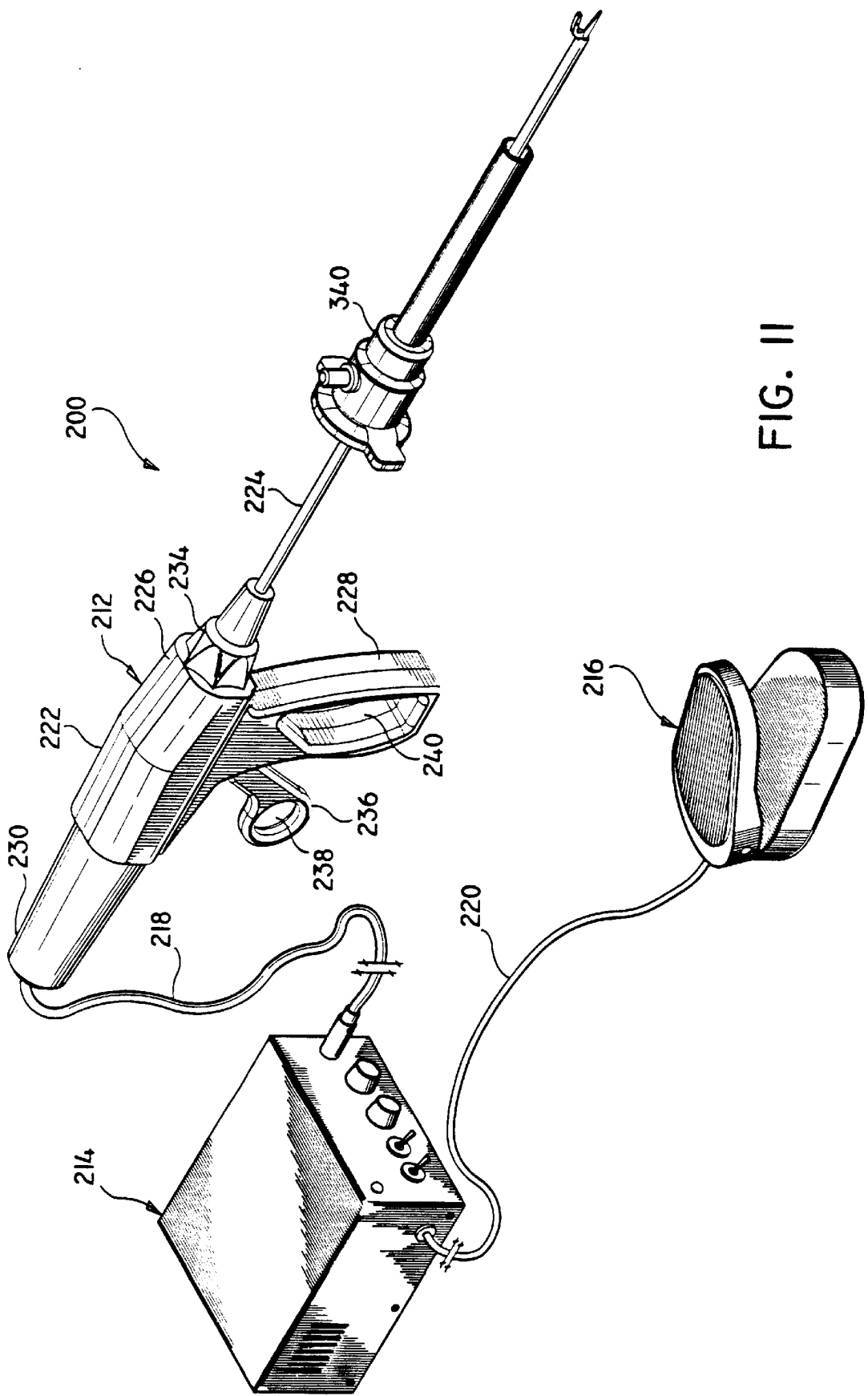
FIG. 11 is a perspective view of an alternate embodiment of the ultrasonic dissection and coagulation system with the ultrasonic instrument inserted partially through a cannula assembly.

FIG. 11 illustrates another alternate embodiment of the ultrasonic instrument in conjunction with an ultrasonic dissection and coagulation system shown generally as 200. Briefly, dissection and coagulation system 200 includes ultrasonic instrument 212, control module 214, and remote actuator 216. Control module 214 is operatively connected to ultrasonic instrument 212 by electrically conductive cable 218 and functions to control the power and frequency of current supplied to ultrasonic instrument 212. Any suitable controller capable of delivering power to ultrasonic instrument 212 can be used. Control module 214 does not form part of the invention and will not be further disclosed herein. Remote actuator 216, e.g., pedal actuator, is operatively connected to control module 214 by electrically conductive cable 220 and can be actuated to initiate the supply of power to ultrasonic instrument 212 via control module 214 to effect vibratory motion of ultrasonic instrument 212 to cut and coagulate tissue.

Figure 12:
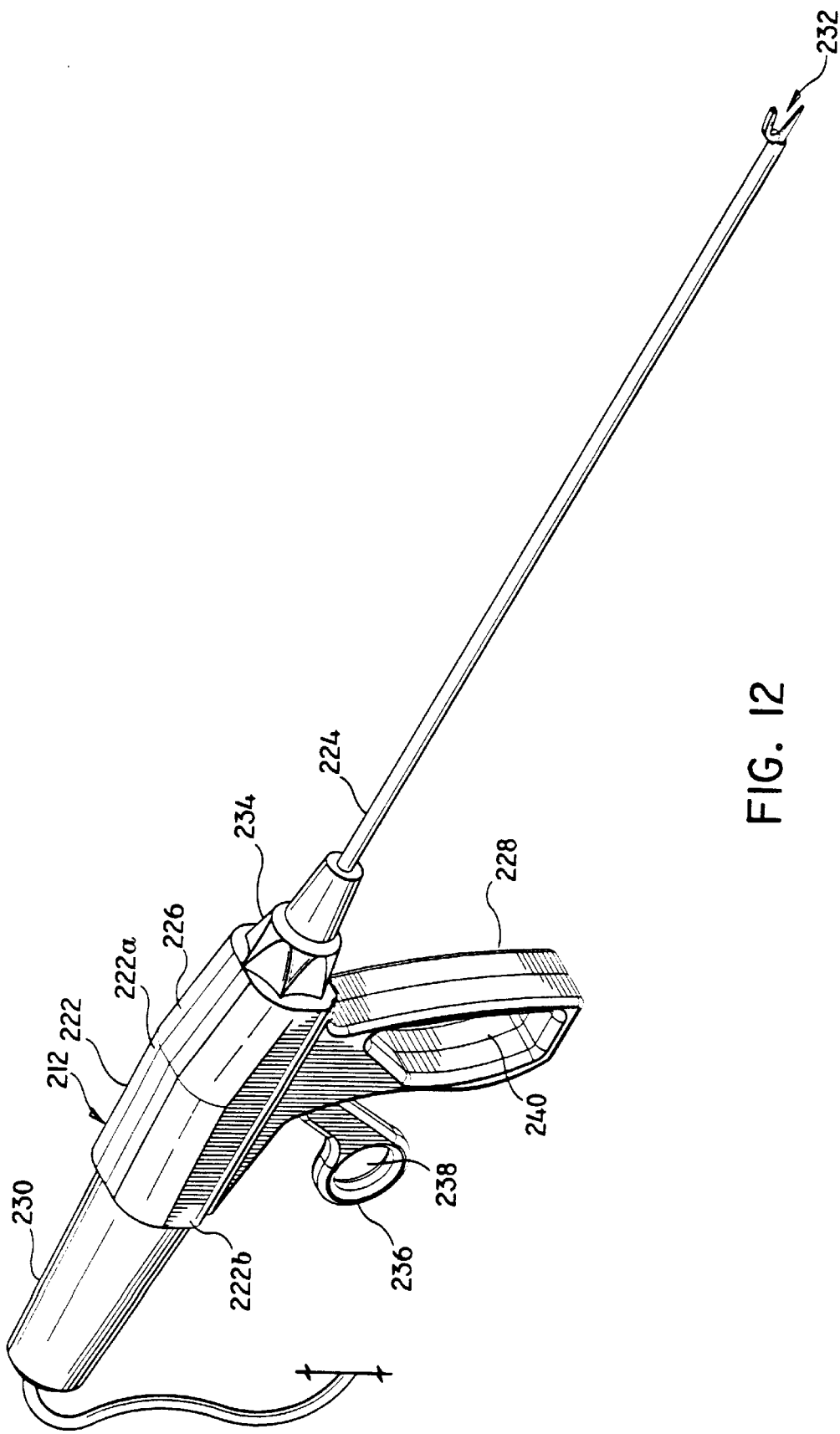
FIG. 12 is a perspective view of the ultrasonic instrument of FIG. 11.

As illustrated in FIG. 12, ultrasonic instrument 212 includes housing 222 and elongated body portion 224 extending distally therefrom. Housing 222 is preferably formed from molded housing half-sections 222a and 222b and includes a barrel portion 226 having a longitudinal axis aligned with the longitudinal axis of body portion 224 and a stationary handle portion 228 extending obliquely from barrel portion 226. Ultrasonic transducer 230 is supported within and extends from the proximal end of housing 222 and is connected to control module 214 via cable 218. Jaw assembly 232 is disposed adjacent the distal end of elongated body portion 224 and is actuated by moving movable handle 236 with respect to stationary handle portion 228. Movable handle 236 and stationary handle portion 228 include openings 238 and 240, respectively, to facilitate gripping and actuation of ultrasonic instrument 212. Elongated body portion 224 is supported within rotatable knob 234 and may be selectively rotated by rotating knob 234 with respect to housing 222 to change the orientation of jaw assembly 232.

FIGS. 13 and 14 illustrate elongated body portion 224 with parts separated. Elongated body portion 224 includes an outer tube 242 which is preferably cylindrical and has a proximally located annular flange 244 dimensioned to engage rotatable knob 234 (FIG. 12) as described below. An elongated actuator tube 246, which is also preferably cylindrical, is configured to be slidably received within outer tube 242 and includes a proximally located annular flange 248 dimensioned to engage coupling member 298 (FIG. 15) which is supported within housing 222 (FIG. 12) and will be described in detail below. Vibration coupler 250 is dimensioned to extend through elongated actuator tube 246 and includes a proximal end 252 having a reduced diameter portion 254 configured to operatively engage ultrasonic transducer 230 and a distal end 256 adapted to be operatively connected to cutting jaw 258. A plurality of silicon rings 251 can be molded or otherwise attached to the nodal points along vibration coupler 250 to seal flow of fluids, e.g., insufflation gas, etc., from between vibration coupler 250 and actuator tube 246. Preferably, cutting jaw 258 includes a proximal threaded extension which is dimensioned to be received within threaded distal end 256 of vibration coupler 250. Alternately, cutting jaw 258 can be formed integrally with vibration coupler 250, or other attachment devices can be used.

A clamp 260 having a clamp body 262 and a tissue contact member 264 removably secured to clamp body 262 is operatively connected to the distal end of actuator tube 246. Tissue contact member 264 is preferably composed of teflon and is preferably removably fastened to clamp body 262 by a tongue and groove fastening assembly (reference numerals 261 and 265, respectively), although other fastening assemblies are also envisioned. Tissue contact member 264 functions to isolate clamp 260 which is preferably metallic from jaw 258, which is also preferably metallic, to prevent metal to metal contact. Tissue contact member 264 also functions to grip tissue positioned between clamp 260 and blade surface 259 of cutting jaw 258 to prevent the tissue from moving with cutting jaw 258 during vibration. Pivot members (pins) 266 located at the proximal end of clamp body 262 are configured to be received within openings 268 formed in the distal end of outer tube 242. A guide slot 270 formed in the distal end of actuator tube 246 permits relative movement between actuator tube 246 and clamp body 262 by allowing pins 266 to move in guide slot 270. A pair of camming members 272 are also formed on clamp body 262 and are positioned to be received within cam slots 274 formed in the distal end of actuator tube 246. Movement of actuator tube 246 and clamp 260 will be described in detail below.

Figures 17, 18:
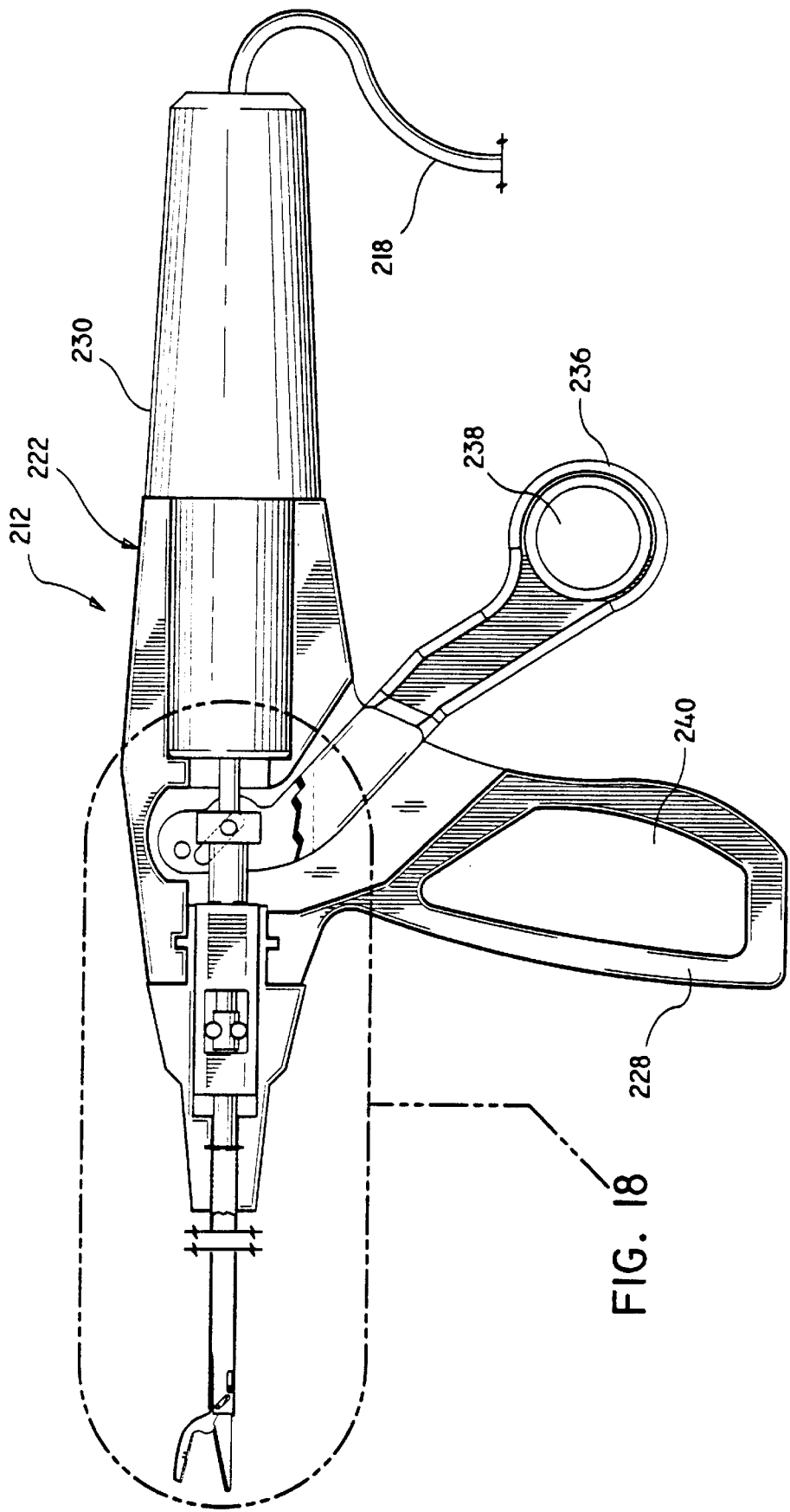
FIG. 17 is a side partial cutaway view of the ultrasonic instrument of FIG. 11 in the open position.
FIG. 18 is an enlarged view of the indicated area of detail of FIG. 17 illustrating the clamp in the open position.
Figure 21:
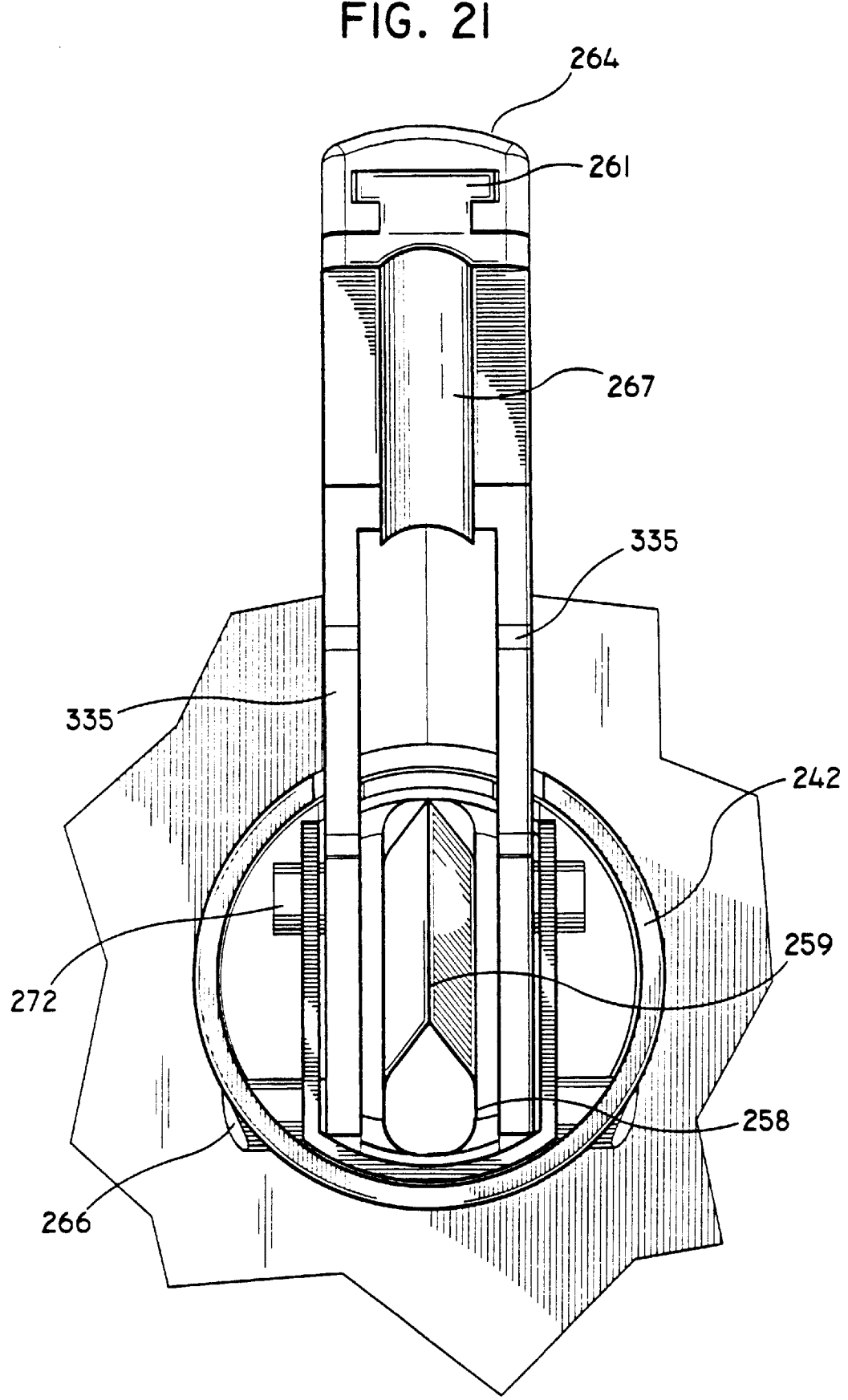
FIG. 21 is a front elevational view taken along line 21—21 of FIG. 18.

Cutting jaw 258 includes a blade surface 259 that is angled downwardly towards its distal end to define a fixed acute angle Θ of from about 10 degrees to about 20 degrees with respect to the longitudinal axis of the elongated body portion 224 and to the axis of vibration. Angled blade surface 259 provides good visibility at the surgical site. Preferably, angle Θ is about 12 degrees. It is also contemplated that greater angles can be utilized such as 20 to 30 degrees. Clamp 260 is movable from an open position in which tissue contact member 264 is spaced from blade surface 259 (FIGS. 17 and 18) to a clamped position in which tissue contact member 264 is in juxtaposed close alignment with blade surface 259 (FIGS. 12 and 13). In the clamped position, note the positioning of tissue contact member 264 with respect to blade surface 259. Actuation of the clamp 260 from the open position to the clamped position will be described in detail below.

Figure 15:
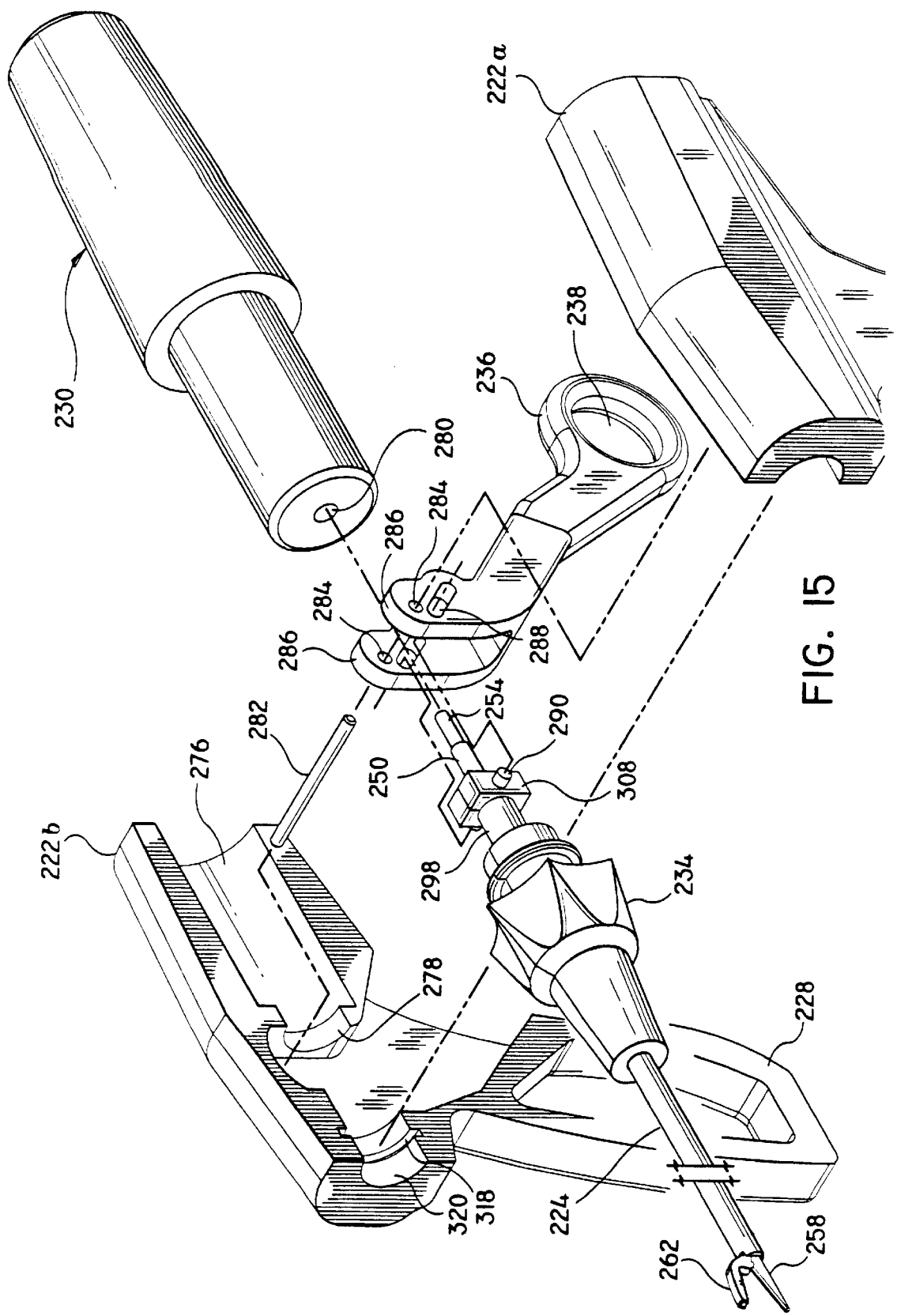
FIG. 15 is a perspective view with parts separated of the handle assembly of the ultrasonic instrument of FIG. 11.
Figure 16:
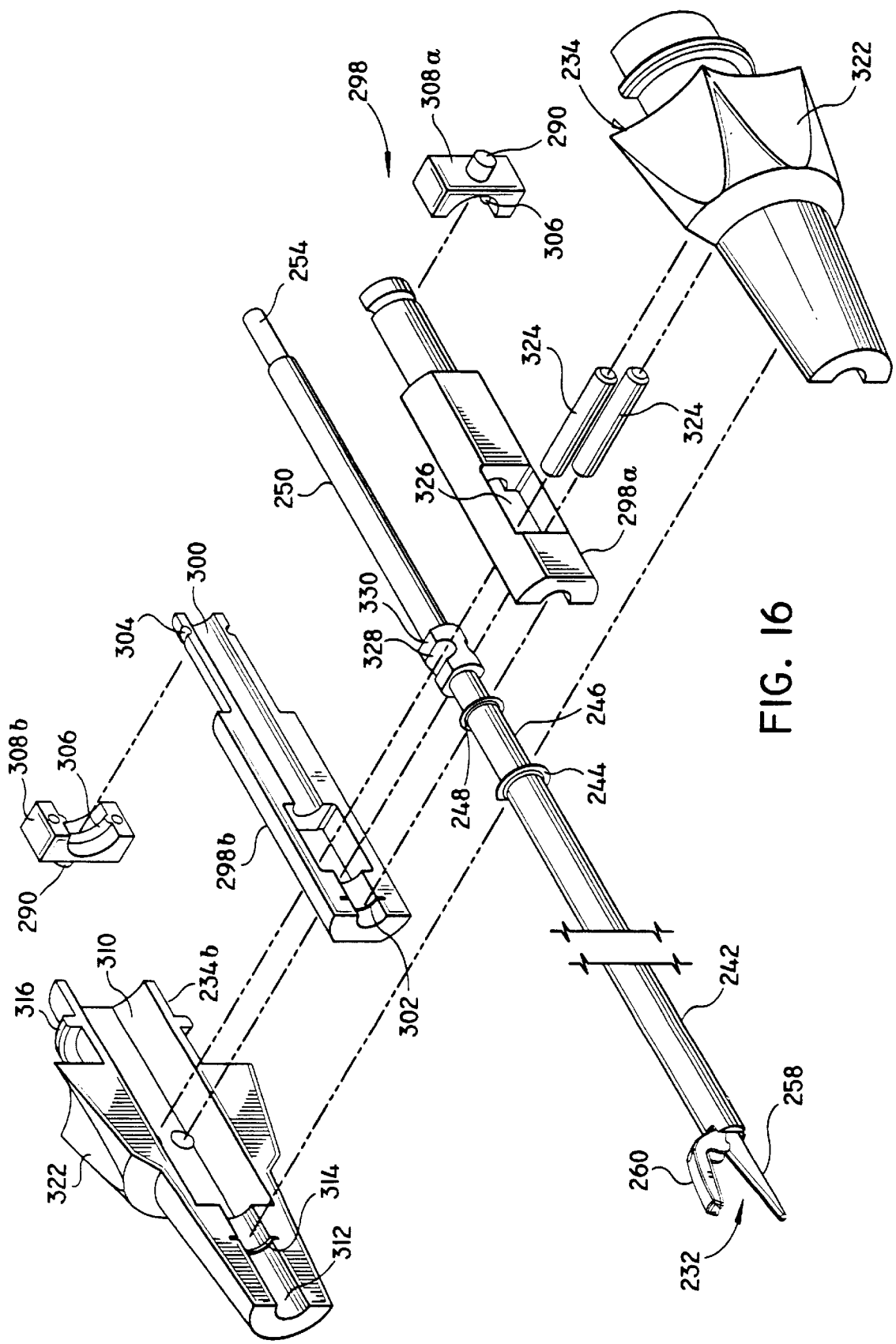
FIG. 16 is a perspective view with parts separated of the rotation assembly of the ultrasonic instrument of FIG. 11.

Referring now to FIGS. 15 and 16, the handle assembly and the rotation assembly will now be discussed. Housing half-sections 222a and 222b define a chamber 276 configured to receive a portion of ultrasonic transducer 230. Chamber 276 has an opening 278 communicating with the interior of housing 222. Ultrasonic transducer 230 includes a bore 280 configured to receive proximal end 254 of vibration coupler 250. In the assembled condition, proximal end 254 extends through opening 278 into bore 280. Movable handle 236 is pivotally connected between housing half-sections 222a and 222b about pivot pin 282 which extends through holes 284 formed in legs 286 of movable handle 236. A cam slot 288 formed in each leg 286 is configured to receive a protrusion 290 projecting outwardly from coupling member 298.

As illustrated in FIG. 16, coupling member 298 operatively connects movable handle 236 to actuator tube 246 and is preferably formed from molded half-sections 298a and 298b to define a throughbore 300 dimensioned to slidably receive the proximal end of vibration coupler 250. Coupling member 298 has an inner distally located annular groove 302 dimensioned to receive annular flange 248 of actuator tube 246 and an outer proximally located annular groove 304. Groove 304 is positioned to receive an annular rib 306 formed on the internal wall of a swivel member 308 (FIG. 15). Swivel member 308 is preferably formed from molded half-sections 308a and 308b and permits rotation of coupling member 298 relative to movable handle 236. Protrusions 290 project outwardly from sidewalls of swivel member 308 and extend through cam slots 288 of movable handle 236.

Referring again to FIGS. 15 and 16, rotation knob 234 is preferably formed from molded half-sections 234a and 234b and includes a proximal cavity 310 for slidably supporting coupling member 298 and a distal bore 312 dimensioned to receive outer tube 242. An annular groove 314 formed in bore 312 is positioned to receive annular flange 244 of outer tube 242. The outer wall of knob 234 has a proximally located annular ring 316 dimensioned to be rotatably received within annular slot 318 formed in opening 320 of housing 222, and a scalloped surface 322 to facilitate gripping of rotatable knob 234. Annular ring 316 permits rotation of knob 234 with respect to housing 222 while preventing axial movement with respect thereto. A pair of cylindrical rods 324 extend between half-sections 234a and 234b through a rectangular opening 326 formed in coupling member 298. Rods 324 engage a pair of concave recesses 328 formed in fitting 330 which is fastened about vibration coupler 250, such that rotation of knob 234 causes rotation of vibration coupler 250 and thus rotation of blade 258 and clamp 260. Alternately, recesses 328 can be monolithically formed with vibration coupler 250.

FIGS. 17–21 illustrate ultrasonic instrument 212 with clamp 260 in the open position. The elongated body 224 which includes clamp 260 and blade 258, and housing 222 which includes handles 228 and 236, are packaged as an integral unit that requires no assembly by the user prior to use, i.e., the vibration coupler 250, the clamp 260, and the blade 258 are non-detachably connected. That is, the user needs only to attach transducer 230 to housing 222 to ready instrument 212 for use. In the open position, movable handle 236 is spaced rearwardly from stationary handle portion 228 and protrusions 290 are positioned in the lower proximal portion of cam slots 288. At the distal end of ultrasonic instrument 212, pivot members 266 are positioned near the distal end of guide slots 270 and camming members 272 are positioned in the upper distal portion of cam slots 274. Tissue contact member 264 of clamp 260 is spaced from blade surface 259 to define a tissue receiving area 332. The proximal end of tissue receiving area 332 is defined by a pair of tissue receiving stops 335 which are preferably integrally formed with clamp body 262 and extend below blade surface 259. Preferably, the distal end of blade 258 is rounded to prevent inadvertent damage to tissue during use of instrument 212. Tissue contact surface 264 is also preferably formed with a concavity 267 to receive tissue therein. Alternatively, the distal end of blade 258 may be formed having any shape which may be suitable to a particular surgical application, i.e., flat, pointed, etc. Moreover, tissue contact surface 264 need not be formed with a concavity but may be flat, angled, etc.

Figure 22:
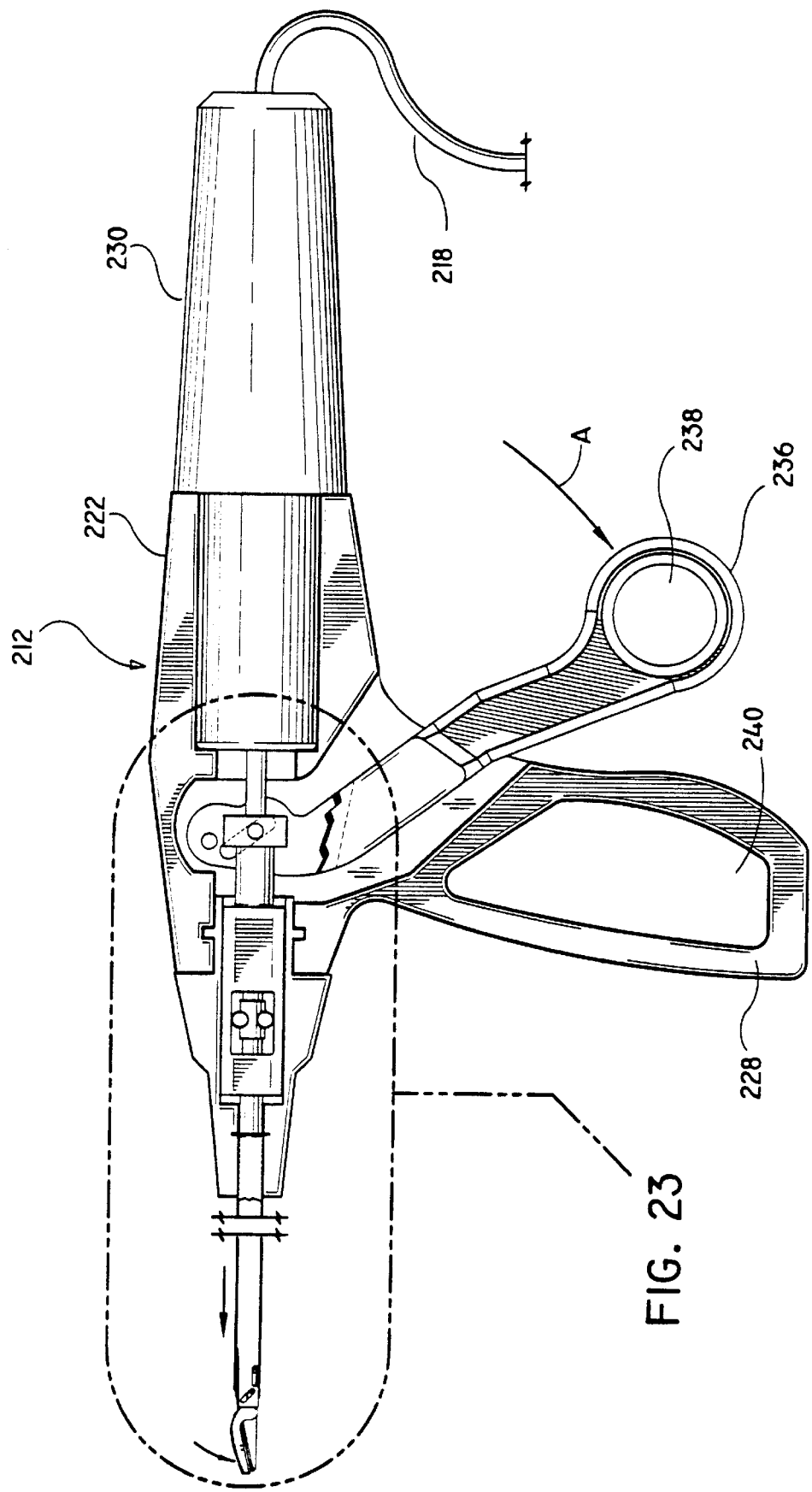
FIG. 22 is a side partial cutaway view of the ultrasonic instrument of FIG. 11 with the clamp in the clamped (closed) position.
Figure 23:
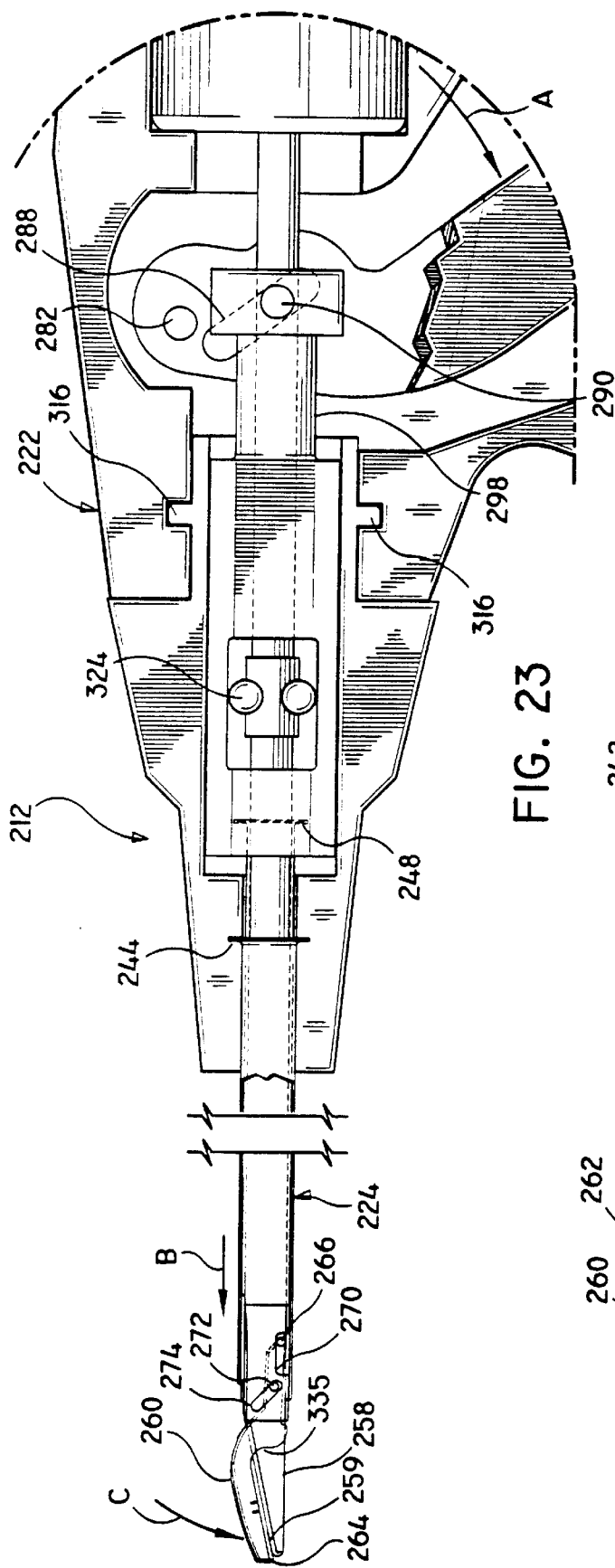
FIG. 23 is an enlarged view of the indicated area of detail of FIG. 22 illustrating the clamp in the closed position.
Figure 24:
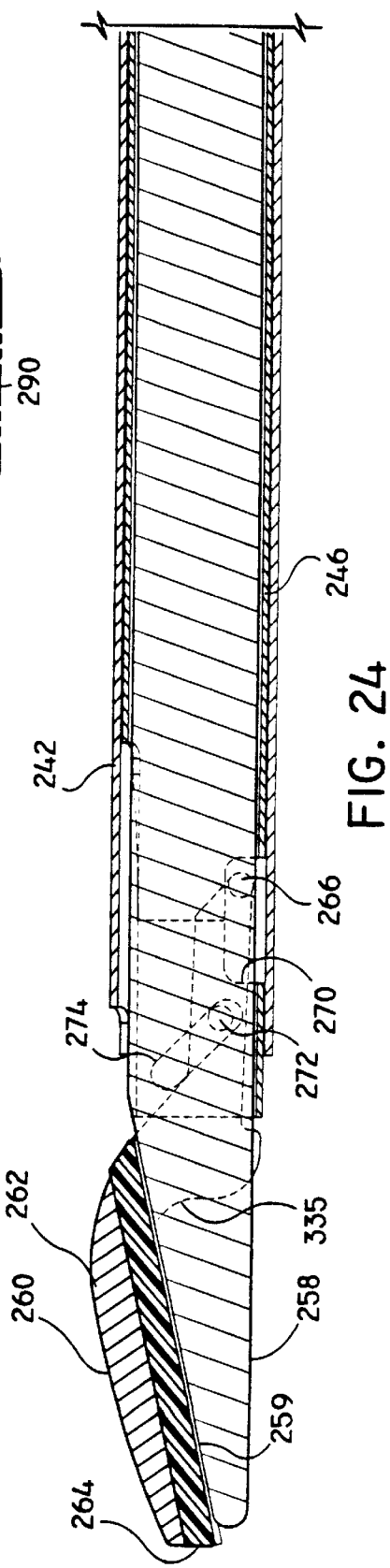
FIG. 24 is a side cross-sectional view of the distal end of the elongated body portion of the ultrasonic instrument of FIG. 11 in the clamped position.

Referring to FIGS. 22–24, when movable handle 236 is pivoted clockwise about pivot member 282 towards stationary handle portion 228, in the direction indicated by arrow "A" in FIG. 22, cam slot 288 engages protrusion 290 of swivel member 308 to advance coupling member 298 distally within cavity 310 of rotation knob 234. Since actuator tube 246 is attached to coupling member 298 by annular flange 248, actuator tube 246 is also advanced distally in the direction indicated by arrow "B" in FIG. 23. Movement of actuator tube 246 distally causes cam slots 274 to move into engagement with camming members 272 to pivot clamp body 262 about pivot members 266, in the direction indicated by arrow "C" in FIG. 23, to move clamp member 262 and tissue contact member 264 into the clamped position. In the clamped position, protrusions 290 are located in a central portion of cam slots 288, pivot members 266 are located near the proximal end of guide slots 270, and camming members 272 are located in the proximal lower portion of cam slots 274.

Figure 25:
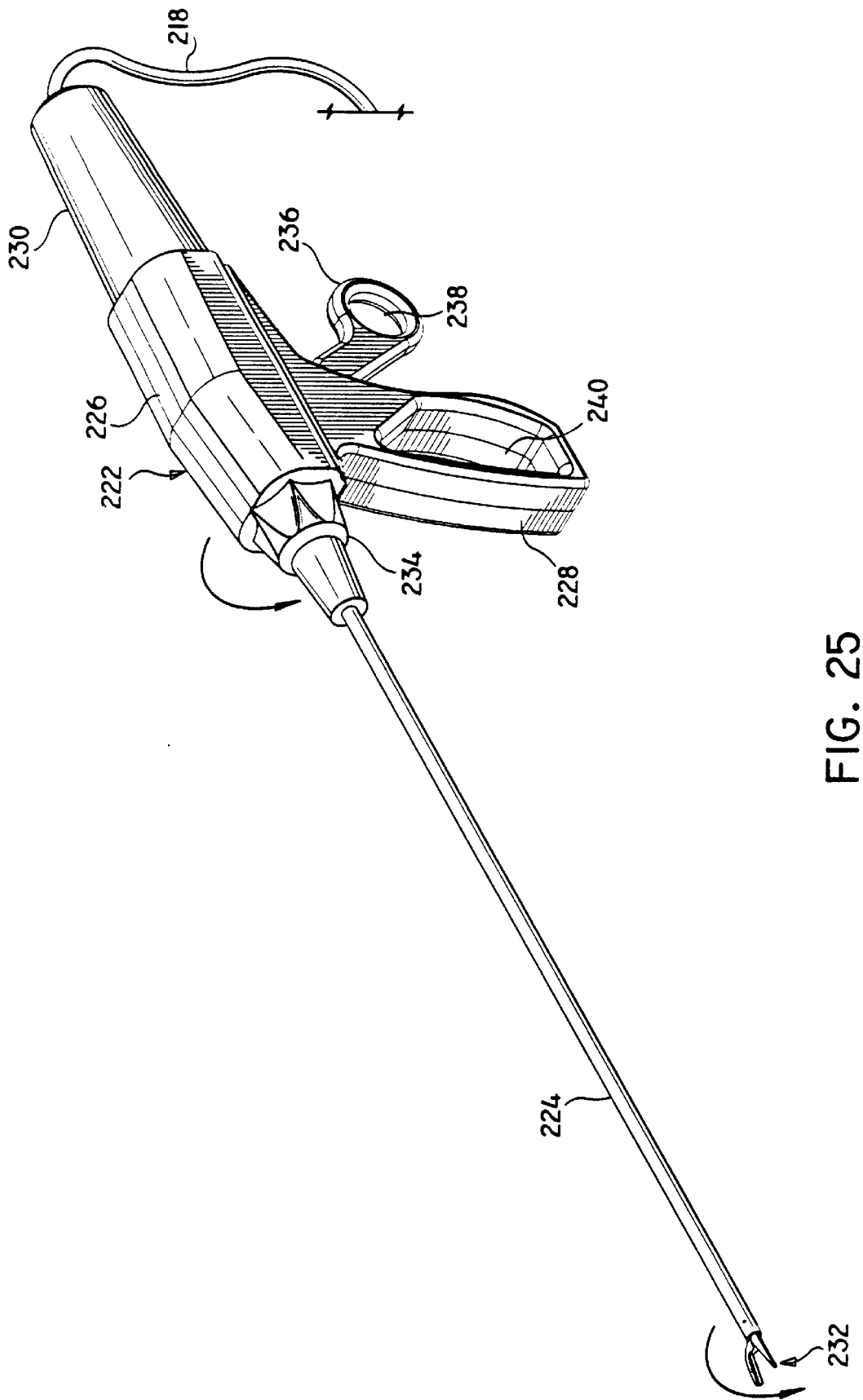
FIG. 25 is a perspective view of the ultrasonic instrument of FIG. 11 with the elongated body portion partially rotated.

Elongated body portion 224 can be freely rotated with respect to housing 222 by rotating rotation knob 234. As illustrated in FIG. 25, rotation of knob 234 in the direction indicated by arrow "D" causes rotation of jaw assembly 232 in the direction indicated by arrow "E". Knob 234 is positioned adjacent housing 222 to facilitate one handed operation of both movable handle 236 and rotation knob 234.

Referring again to FIG. 11, elongated body portion 224 is dimensioned to extend through a trocar assembly 340, and is preferably dimensioned to extend through a 5 mm trocar assembly. During use, elongated body portion 224 is slid through trocar assembly 340 with jaw assembly 232 in the clamped or closed position to a position adjacent to tissue (not shown) to be dissected and/or coagulated. An optical unit (not shown) can also be positioned adjacent the surgical site to facilitate viewing of the procedure. Jaw assembly 232 is opened and tissue to be dissected and/or coagulated is positioned within tissue receiving area 332 (See also FIG. 19). Tissue receiving stops 335 prevent tissue from moving past the proximal end of blade surface 259. Next, jaw assembly 232 is closed to clamp tissue between tissue contact member 264 and blade surface 259. Power is supplied to ultrasonic instrument 212 via control module 214 to initiate vibration of blade 258 to effect dissection and coagulation of tissue. Because of the angle of blade surface 259, the contact pressure applied by blade surface 259 on the tissue being dissected is increased as the force applied to instrument 212 is increased. It is noted that after use, instrument 212 can be autoclaved and used again.

Figure 26:
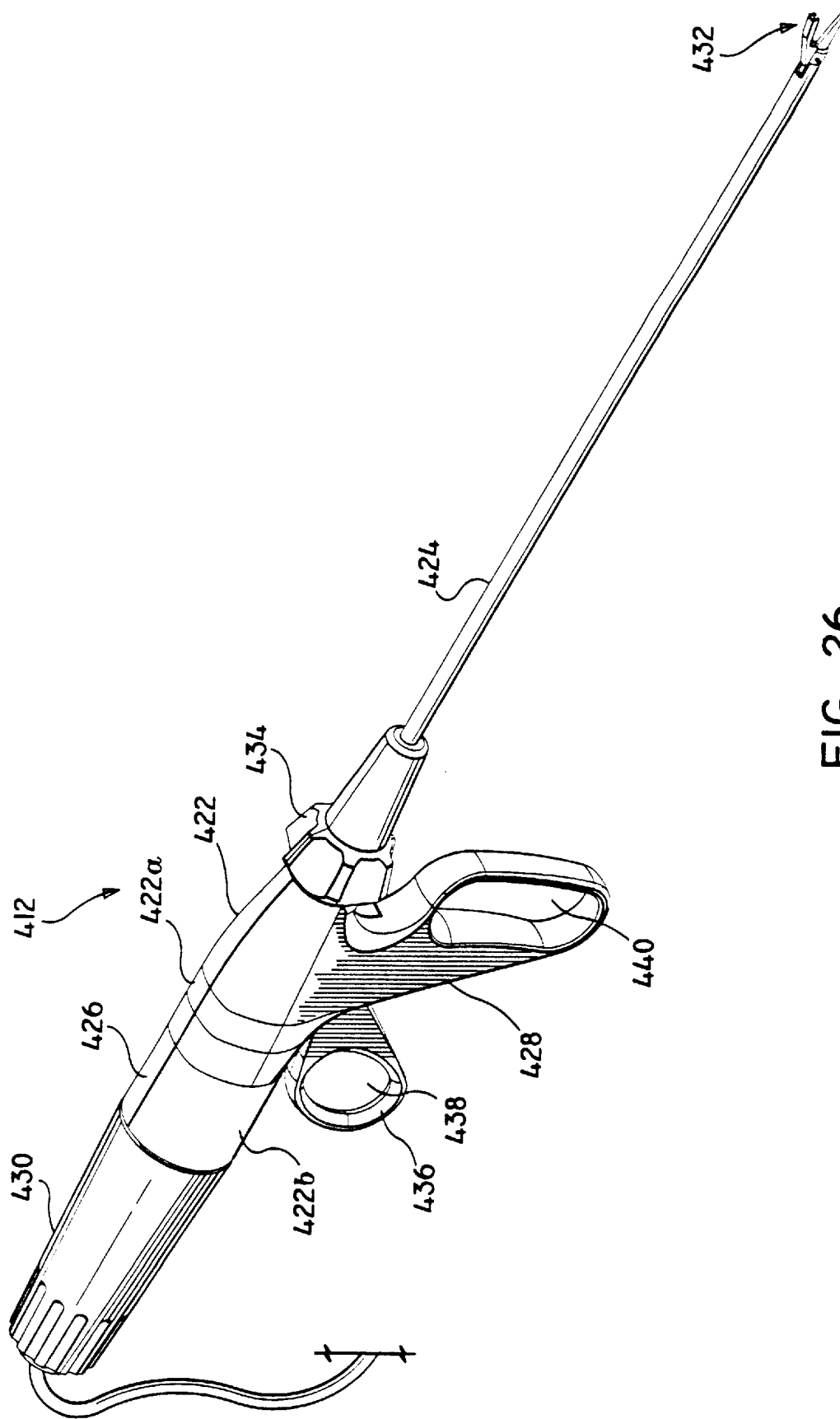
FIG. 26 is a side perspective view of another alternate embodiment of the ultrasonic instrument in the open position.

FIG. 26 illustrates another alternate embodiment of the ultrasonic instrument, shown generally as 412. Ultrasonic instrument 412 includes housing 422 and elongated body portion 424 extending distally from housing 422. Housing 422 is preferably formed from molded housing half-sections 422a and 422b and includes a barrel portion 426 having a longitudinal axis aligned with the longitudinal axis of body portion 424 and a stationary handle portion 428 extending obliquely from barrel portion 426. Ultrasonic transducer 430 is supported within and extends from the proximal end of housing 422 and includes a proximal fluted portion 431 configured to engage an attachment device to facilitate attachment and removal of transducer 430 from instrument 412. Jaw assembly 432 is disposed adjacent the distal end of elongated body portion 424 and is actuated by moving movable handle 436 with respect to stationary handle portion 428. Movable handle 436 and stationary handle portion 428 include openings 438 and 440, respectively, to facilitate gripping and actuation of ultrasonic instrument 412. Elongated body portion 424 is supported within rotatable knob 434 and may be selectively rotated by rotating knob 434 with respect to housing 422 to change the orientation of jaw assembly 432.

Figure 27:
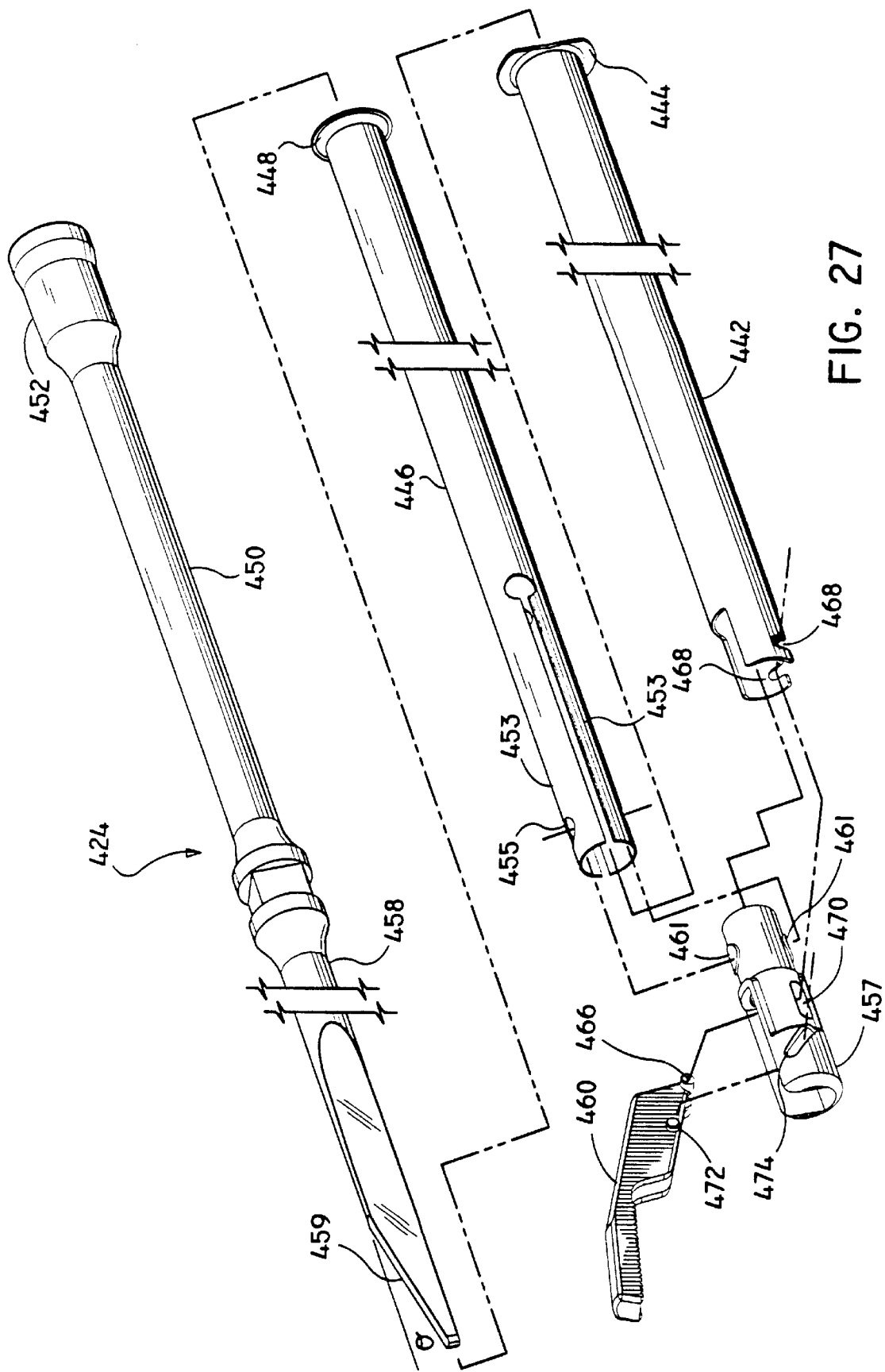
FIG. 27 is a perspective view of the elongated body portion of the ultrasonic instrument shown in FIG. 26.

FIG. 27 illustrates elongated body portion 424 with parts separated. Elongated body portion 424 includes an outer tube 442 which is preferably cylindrical and has a proximally located annular flange 444 dimensioned to engage rotatable knob 434 (FIG. 26). An elongated actuator tube 446, which is also preferably cylindrical, is configured to be slidably received within outer tube 442 and includes a proximally located annular flange 448 dimensioned to engage coupling member 498 (FIG. 29) which is supported within housing 422 (FIG. 26). Although not shown, it is contemplated that a portion of actuator tube 446 and a portion of outer tube 442 adjacent flange 444 flares outwardly to provide additional clearance for vibration coupler 450. Vibration coupler 450 is dimensioned to extend through elongated actuator tube 446 and includes an enlarged proximal end 452 having a bore (not shown) configured to operatively engage ultrasonic transducer 430. The distal end of actuator tube 446 includes a pair of resilient arms 453 having distally located openings 455. The openings 455 are dimensioned to receive protrusions 461 formed on an adaptor 457. Arms 453 are flexible outwardly and engage adaptor 457. Cutting jaw 458 is monolithically formed with vibration coupler 450. Alternately, cutting jaw 458 and vibration coupler 450 can be formed separately and fastened together using any known connector, e.g., screw threads, friction fit, etc. Although not shown, a plurality of sealing rings can be molded or otherwise attached to the nodal points along vibration coupler 450 to seal between vibration coupler 450 and actuator tube 446.

Figure 28A:
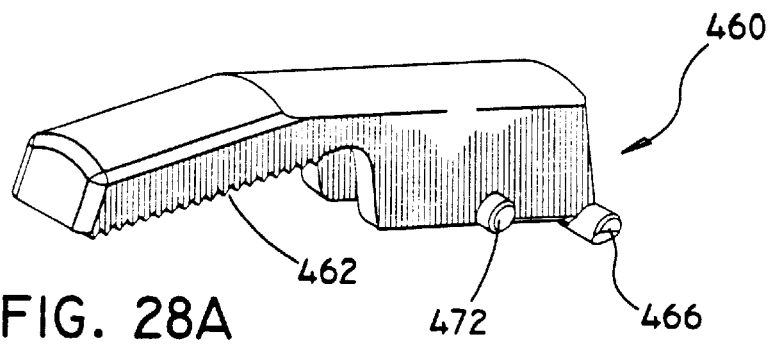
FIG. 28A is a side perspective view of the clamp of the ultrasonic instrument shown in FIG. 26.
Figure 28B:
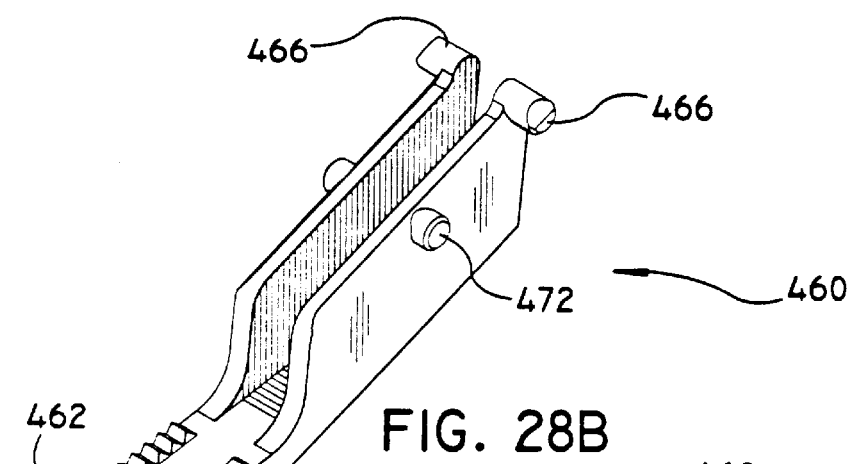
FIG. 28B is a side perspective view of the tissue contact surface of the clamp shown in FIG. 28A.
Figure 28C:
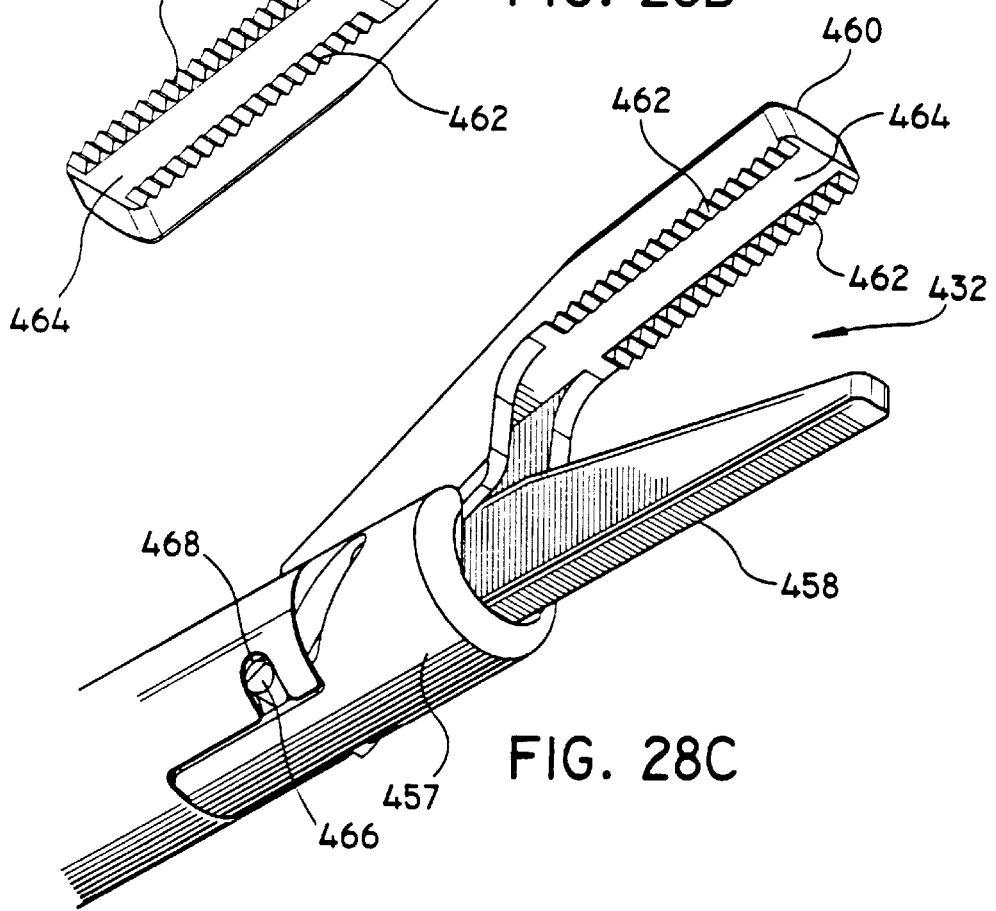
FIG. 28C is a side perspective view of the distal end of the elongated body portion of the ultrasonic instrument shown in FIG. 26.

Referring also to FIGS. 28A–C, a clamp 460 is operably connected to adaptor 457. Clamp 460 preferably includes a pair of longitudinally extending rows of teeth 462 which are spaced from each other a distance which permits cutting jaw 458 to be positioned between the rows of teeth 462. Teeth 462 function to grip tissue when the jaw assembly 432 is in a closed position to prevent tissue from moving with respect to cutting jaw 458 during vibration of the cutting jaw.

Pivot members or pins 466 are formed at the proximal end of clamp 460 and are configured to be received within open ended slots 468 in the distal end of outer tube 442. Slots 468 are open on one side thereof to permit clamp 460 to be retained therein. A longitudinally extending guide slot 470 formed in adaptor 457 is dimensioned to slidably receive pivot pin 466 and permit relative movement between adaptor 457 and clamp 460. A pair of camming members 472 are also formed on clamp 462 and are positioned to be received in cam slots 474 formed in the adaptor 457.

Cutting jaw 458 includes blade surface 459 which is flat and angled downwardly toward its distal end to define a fixed acute angle $\Theta$ of from about 10 degrees to about 20 degrees with respect to the longitudinal axis of the elongated body portion 424 and to the axis of vibration. The angled blade surface provides for good visibility at the surgical site. Preferably, angle $\Theta$ is about 12 degrees, but greater angles such as 20 to 30 degrees are also envisioned. Alternately, blade surface 459 may be other than flat, e.g., sharpened, rounded, etc.

Clamp 460 is movable relative to cutting jaw 458 from an open position (FIG. 28C) in which tissue contact surface 464 of clamp 460 is spaced from blade surface 459 to a closed or clamped position (FIG. 35) in which tissue contact surface 464 is in juxtaposed closer alignment with blade surface 459. In the clamped position, note the positioning of tissue contact surface 464 with respect to blade surface 459. Actuation of clamp 460 from the open position to the clamped position will be described in detail below.

Figure 29:
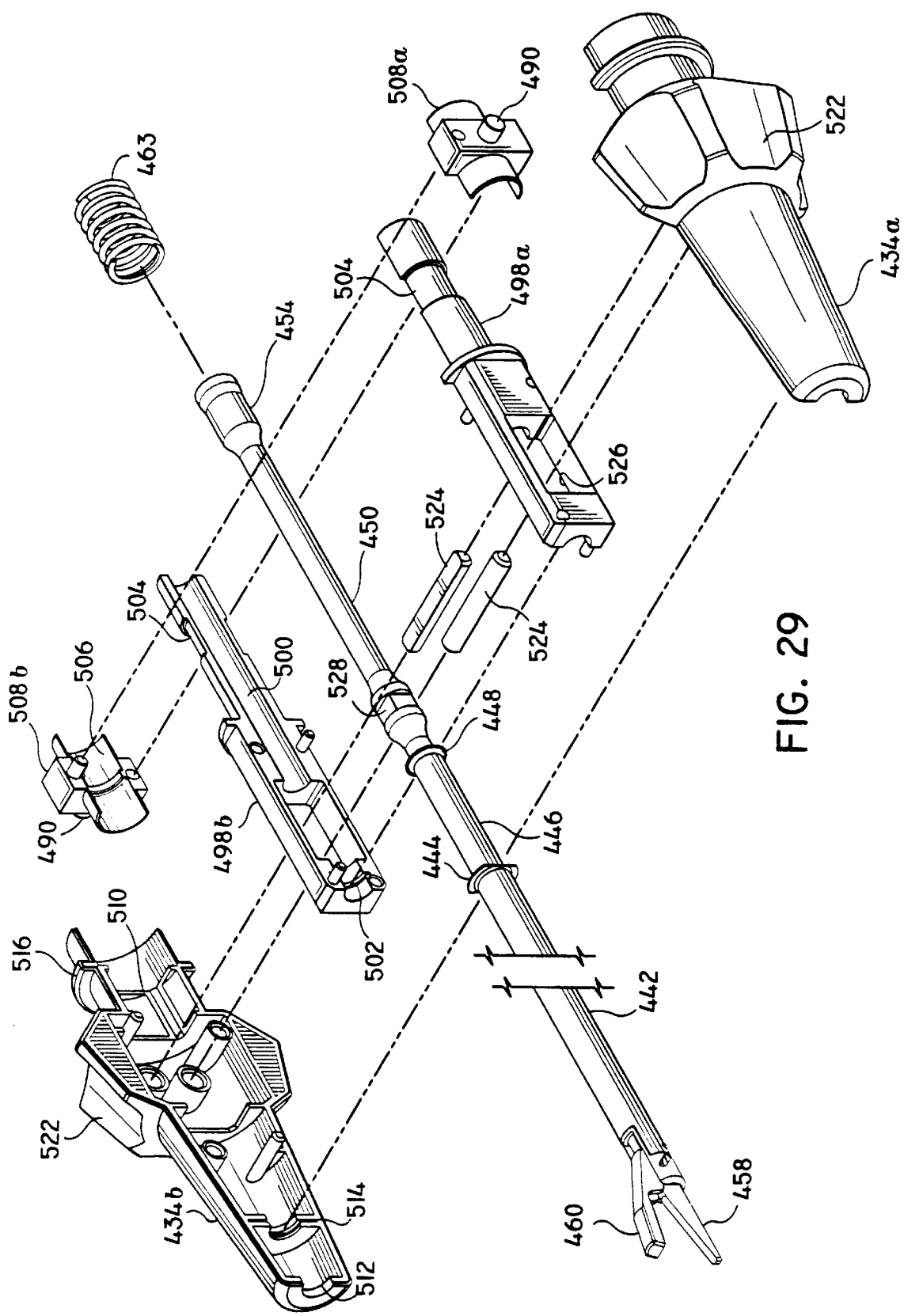
FIG. 29 is a side perspective view of the elongated body portion and rotation assembly of the ultrasonic instrument shown in FIG. 26.
Figure 30:
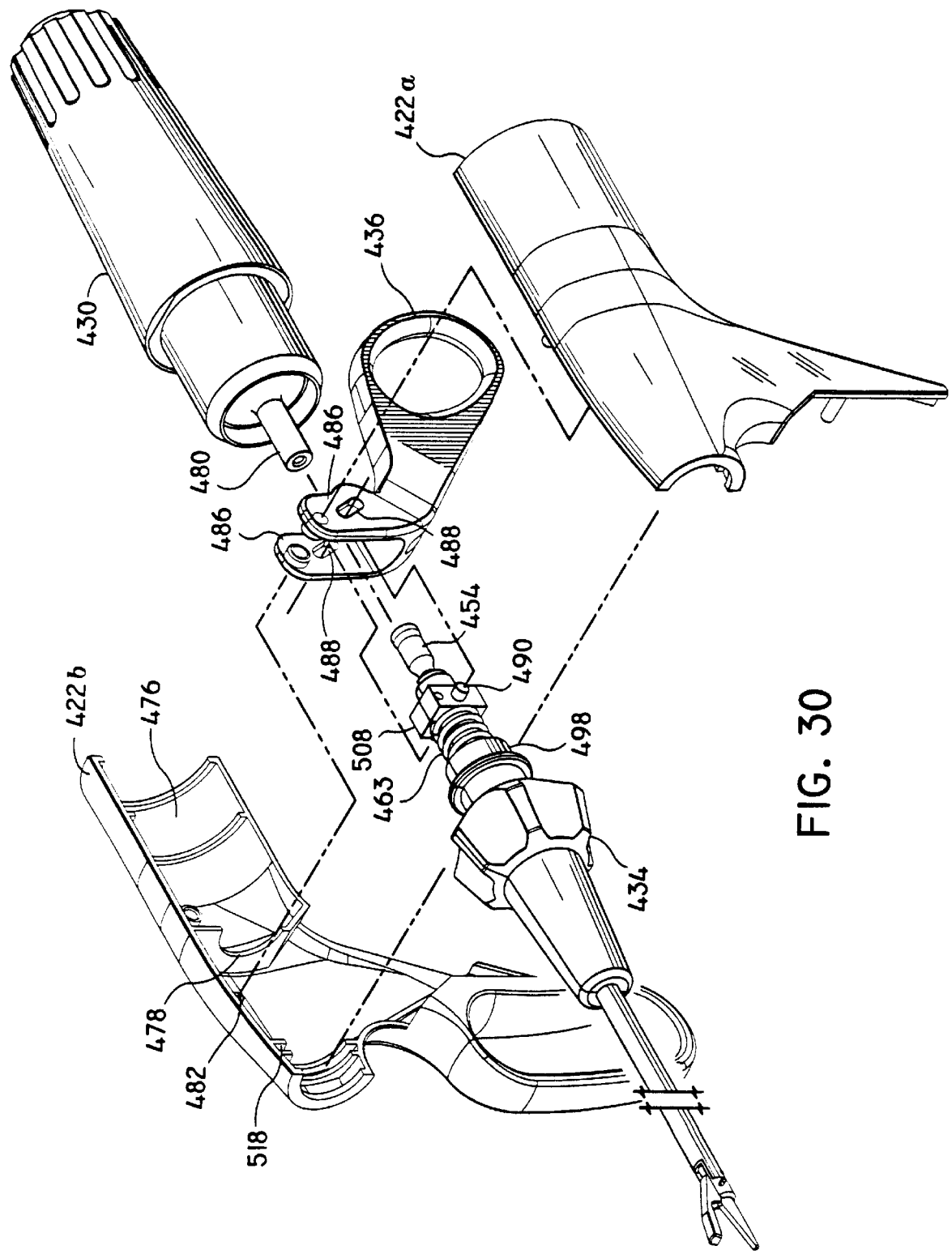
FIG. 30 is a side perspective view of the handle assembly and transducer assembly of the ultrasonic instrument shown in FIG. 26.

Referring to FIGS. 29 and 30, housing half-sections 422a and 422b define a chamber 476 configured to house a portion of ultrasonic transducer 430. Chamber 476 has an opening 478 communicating with the interior of housing 422. Ultrasonic transducer 430 includes a cylindrical stem 480 configured to be received in an opening in proximal end 454 of vibration coupler 450. In the assembled condition, proximal end 454 extends through opening 478 into engagement with cylindrical stem 480. Movable handle 436 is pivotally connected between housing half-sections 422a and 422b about pivot pin members 482 which are monolithically formed with housing half-sections 422a. A cam slot 488 formed in each leg 486 is configured to receive a protrusion 490 projecting outwardly from coupling member 498.

Coupling member 498 operatively connects movable handle 436 to actuator tube 446 and is preferably formed from molded half-sections 498a and 498b to define a throughbore 500 dimensioned to slidably receive the proximal end of vibration coupler 450. Coupling member 498 has an inner distally located annular groove 502 dimensioned to receive annular flange 448 of actuator tube 446 and an outer proximally located annular groove 504 positioned to receive an annular projection 506 formed on the internal wall of swivel member 508. The projection 506 of swivel member 508 is movable through groove 504 to permit relative longitudinal movement between coupling member 498 and swivel member 508. A spring 463 is positioned between coupling member 498 and swivel member 508 to bias the swivel member 508 proximally with respect to coupling member 498. Swivel member 508 is preferably formed from molded half-sections 508a and 508b and permits rotation of coupling member 498 relative to movable handle 436. Protrusions 490 project outwardly from sidewalls of swivel member 508 and extend through cam slots 488 of movable handle 436.

Figure 31A:
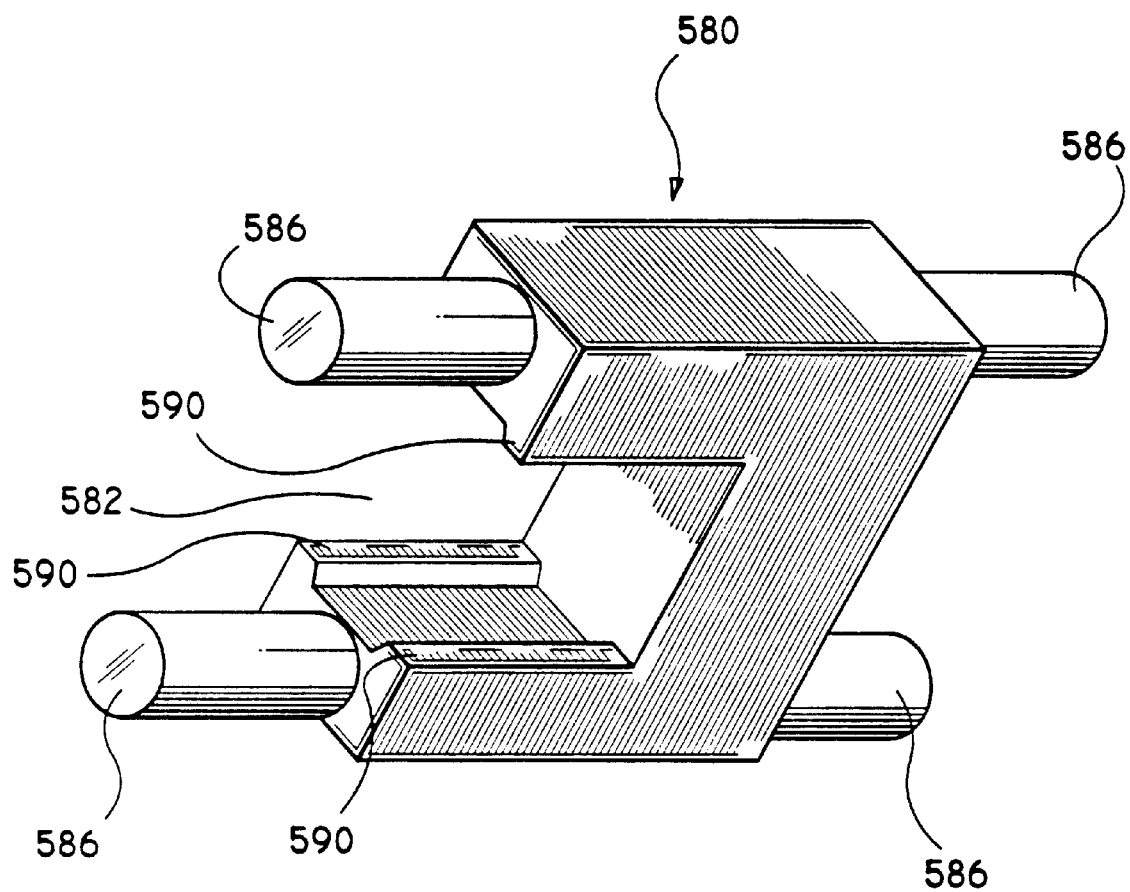
FIG. 31A is an enlarged perspective view of a C-clip locator for the vibration coupler.

Rotation knob 434 is preferably formed from molded half-sections 434a and 434b and includes a proximal cavity 510 for slidably supporting coupling member 498 and a distal bore 512 dimensioned to receive outer tube 442. An annular groove 514 formed in bore 512 is positioned to receive annular flange 444 of outer tube 442. The outer wall of knob 434 has a proximally located annular ring 516 dimensioned to be rotatably received within annular slot 518 formed in housing 422, and a scalloped surface 522 to facilitate gripping of rotatable knob 434. Annular ring 516 permits rotation of knob 434 with respect to housing 422 while preventing axial movement with respect thereto. A pair of rods or pins 524 extend between half-sections 434a and 434b through a rectangular opening 526 formed in coupling member 498. Rods 524 engage a pair of flattened surfaces 528 formed on vibration coupler 450, such that rotation of knob 434 causes rotation of vibration coupler 450 and thus rotation of blade 458 and clamp 460. Alternately, to provide additional surface contact, instead of pins 524, a C-clip shown generally as 580 in FIG. 31A is provided. C-clip 580 mounted by pins 586 has an opening 582 to receive the vibration coupler 450. The flats of vibration coupler 450 contact the four flat regions 590 of the C-clip 580.

A retainer ring (not shown) may be mounted on ribs 492 of housing 422 (FIG. 32) to provide additional support for actuator tube 446. In this embodiment, tube 446 would extend proximally past ribs 492.

FIGS. 31–34 illustrate ultrasonic instrument 412 with clamp 460 in the open position. The elongated body 424 which includes clamp 460 and blade 458, and housing 422 which includes handles 428 and 436, are packaged as an integral unit that requires no assembly by the user prior to use, i.e., vibration coupler 450, clamp 460, and blade 458 are non-detachably connected. That is, the user needs only to attach transducer 430 to housing 422 to ready instrument 412 for use. In the open position, movable handle 436 is spaced rearwardly from stationary handle portion 428 and protrusions 490 are positioned in the lower proximal portion of cam slots 488. At the distal end of ultrasonic instrument 412, pivot members 466 are positioned near the distal end of guide slots 470 and camming members 472 are positioned in the upper distal portion of cam slots 474. Tissue contact surface 464 of clamp 460 is spaced from blade surface 459 to define a tissue receiving area 532. The proximal end of tissue receiving area 532 is defined by a pair of tissue receiving stops 535 which are preferably integrally formed with clamp 460 and extend below blade surface 459. Preferably, the distal end of blade 458 is devoid of sharp edges which may cause inadvertent damage to tissue during use of instrument 412. Alternately, the distal end of blade 458 may be formed having any shape which may be suitable to a particular surgical application, i.e., flat, pointed, etc.

Figure 35:
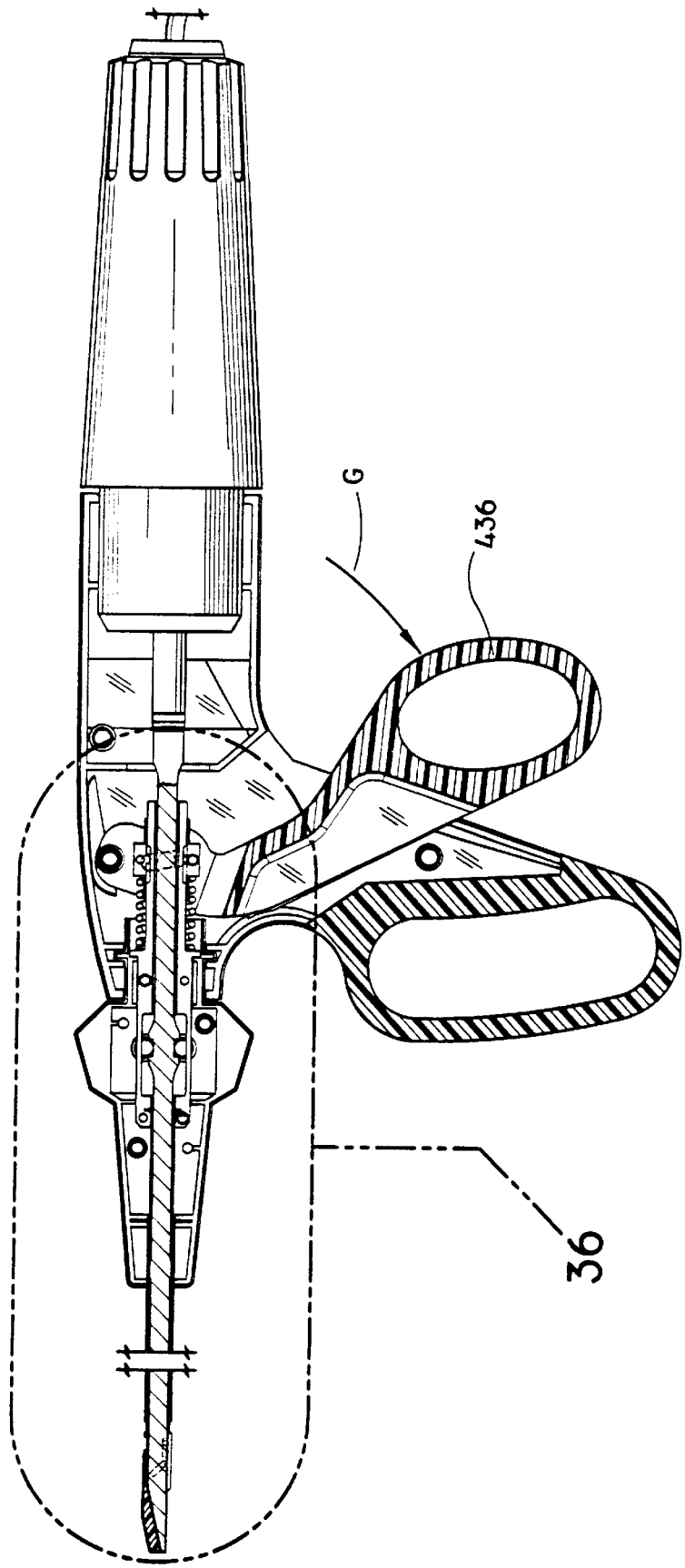
FIG. 35 is a side partial cross-sectional view of the ultrasonic instrument of FIG. 26 in the closed position.
Figure 36:
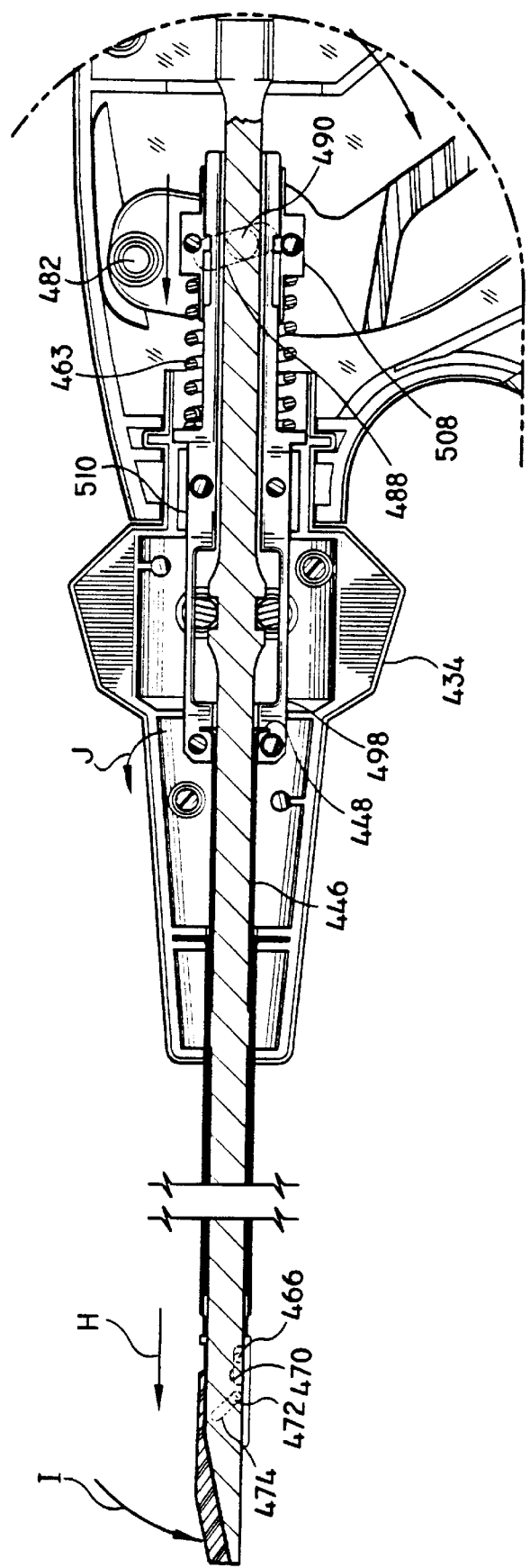
FIG. 36 is an enlarged view of the indicated area of detail of FIG. 35 illustrating the clamp in the closed position.

Referring to FIGS. 35 and 36, when movable handle 436 is pivoted clockwise about pivot member 482 towards stationary handle portion 428, in the direction indicated by arrow "G" in FIG. 35, cam slot 488 engages protrusion 490 of swivel member 508 to advance coupling member 498 distally within cavity 510 of rotation knob 434. Since actuator tube 446 is attached to coupling member 498 by annular flange 448, actuator tube 446 is also advanced distally in the direction indicated by arrow "H" in FIG. 36. Movement of actuator tube 446 distally causes cam slots 474 to move into engagement with camming members 472 to pivot clamp body 462 about pivot members 466, in the direction indicated by arrow "I" in FIG. 36, to move clamp member 462 and tissue contact member 464 into the clamped position. Spring 463 prevents over clamping of tissue by permitting relative movement between swivel member 508 and coupling member 498 after a predetermined clamping pressure has been applied against blade 458. In the clamped position, protrusions 490 are located in a central portion of cam slots 488, pivot members 466 are located near the proximal end of guide slots 470, and camming members 472 are located in the proximal lower portion of cam slots 474.

Elongated body portion 424 can be freely rotated with respect to housing 422 by rotating rotation knob 434. Rotation of knob 434 in the direction indicated by arrow "J" causes rotation of jaw assembly 432 in the direction indicated by arrow "K". Knob 434 is positioned adjacent housing 422 to facilitate one handed operation of both movable handle 436 and rotation knob 434.

Figure 37:
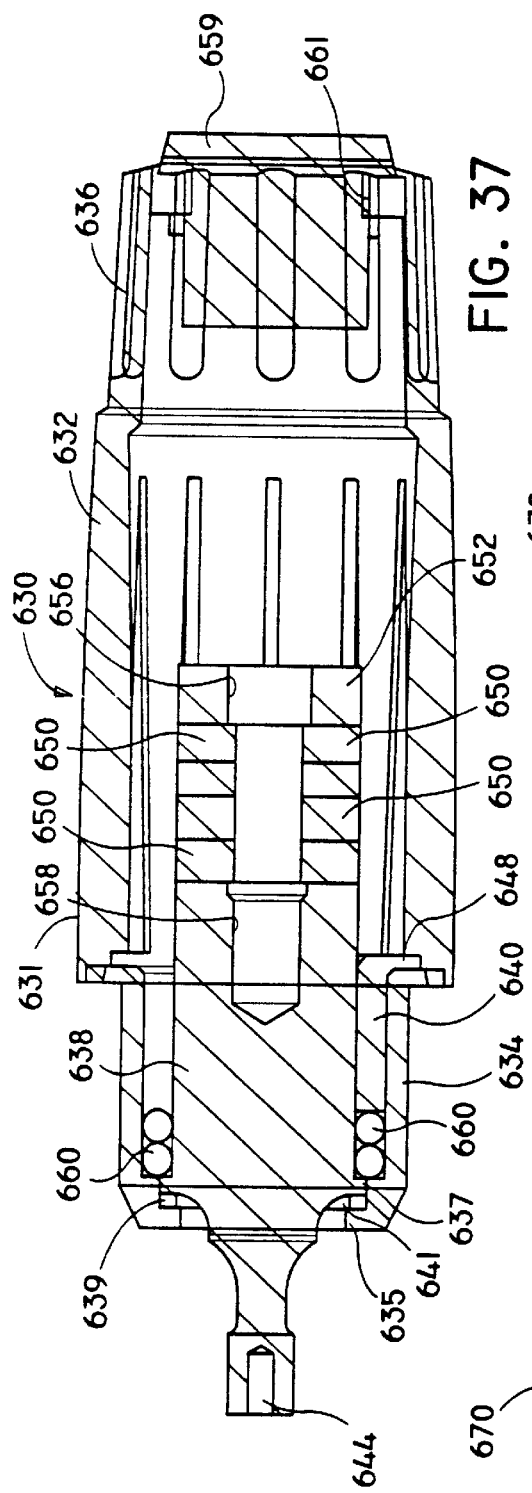
FIG. 37 is a side cross-sectional view of an alternate embodiment of the ultrasonic transducer of FIG. 11.

Referring now to FIG. 37, an alternate embodiment of the ultrasonic transducer is shown generally as 630. Ultrasonic transducer 630 includes a housing 631 having a proximal housing portion 632 and a distal housing portion 634. Proximal housing portion 632 has a scalloped section 636 adjacent its proximal end and distal housing portion 634 has a radial portion 635 that extends inwardly to partially cover transducer horn 638. Transducer horn 638 includes a shoulder portion 637 positioned adjacent to radial portion 635 of distal housing portion 634 to define a recess 651 for receiving a washer 639. Washer 639 functions to seal the space between radial portion 635 and transducer horn 638 and, to prevent transducer horn 638 from longitudinal contact with distal housing portion 634. Shoulder portion 637 of transducer horn 638 does contact an inner wall of distal housing portion 634 to assist in maintaining the longitudinal alignment of transducer horn 638 within housing 631. The distal end of transducer horn 638 includes a threaded bore 644 dimensioned to engage a reduced diameter portion of vibration coupler 650. A pair of spacers 640 are positioned between transducer horn 638 and distal housing portion 634. Each spacer 640 includes an annular flange 648 which is sonically welded and hermetically sealed between proximal and distal housing portions 632 and 634. The proximal end of each spacer 640 engages an O-ring of a pair of O-rings to compress the O-rings to provide a seal between distal housing portion 634 and transducer horn 638 and to provide radial support for transducer horn 638. The spacer O-ring combination further maintains transducer horn 638 in a position to compress washer 639 in recess 641. Piezoelectric crystals 650 are secured in contact with the proximal end of transducer horn 638 by a backing plate 652 and a screw (not shown) which is inserted through an opening 656 in backing plate 652 into threaded bore 658 formed in the proximal end of transducer horn 638. Wires (not shown) from crystals 650 extend to a connector 659 which may be threadably received in an opening 661 in proximal housing portion 632.

Figure 38B:
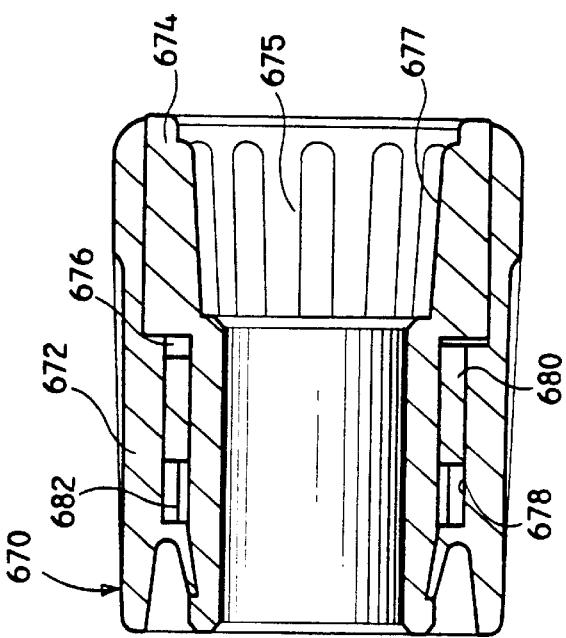
FIG. 38B is a side cross-sectional view taken along section line 38B—38B of FIG. 37.
Figure 38A:
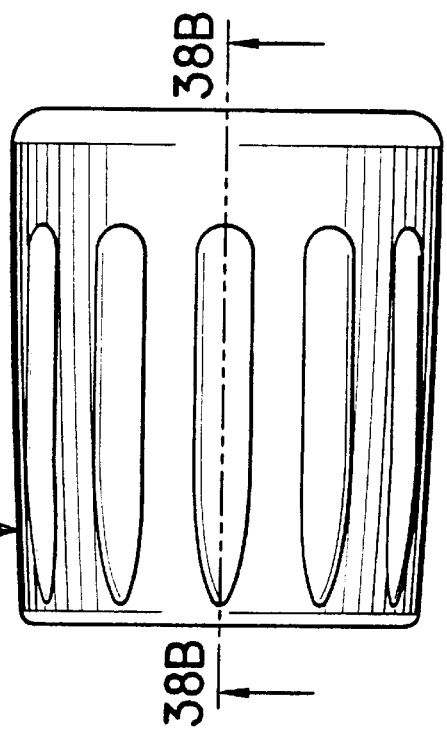
FIG. 38A is a side view of a torque wrench assembly in engagement with the ultrasonic transducer of FIG. 37A.
Figure 38D:
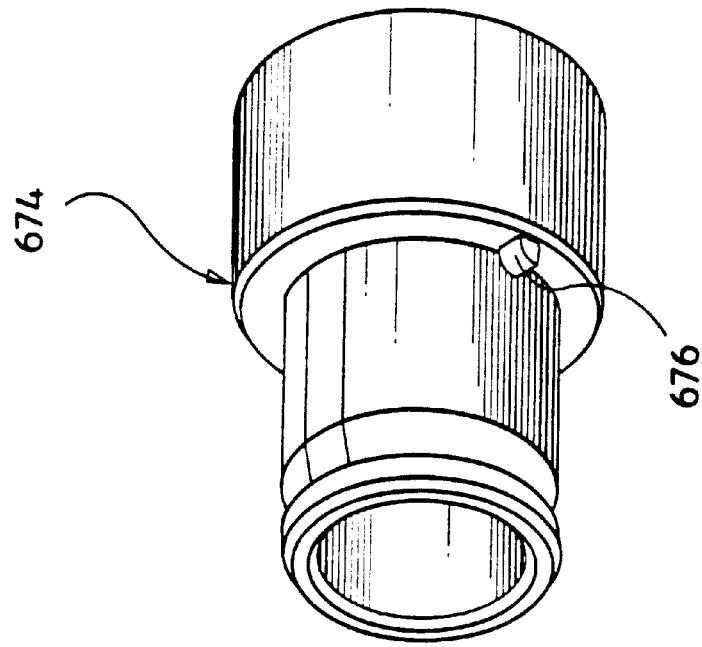
FIG. 38D is a perspective view of the driver member of the torque wrench assembly shown in FIG. 38B.
Figure 38C:
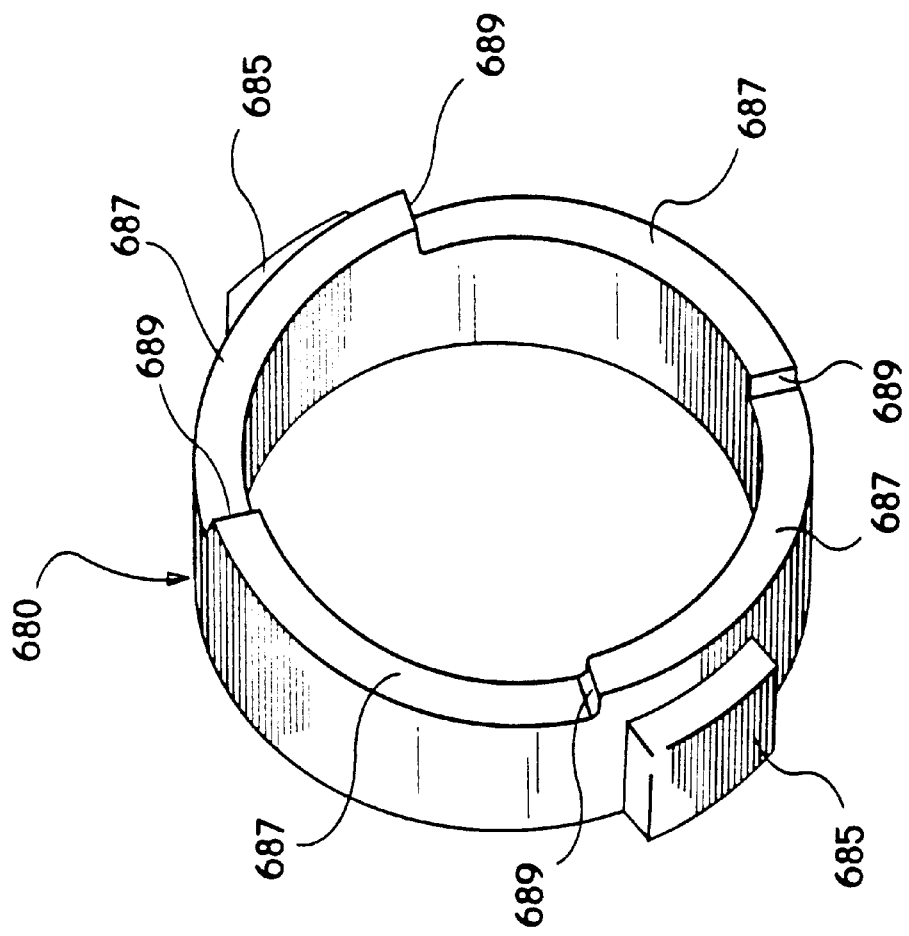
FIG. 38C is a perspective view of the cam member of the torque wrench assembly shown in FIG. 38B.

FIGS. 38A and 38B illustrate a torque wrench assembly shown generally as 670. Torque wrench assembly 670 includes outer housing 672 and inner drive member 674. Inner drive member 674 has an opening 675 having an inner scalloped wall 677 configured to matingly engage scalloped section 636 of housing 631. Inner drive member 674 also includes a projection or bump 676 (see FIG. 38D) which extends into a cylindrical recess 678 defined between inner driver member 674 and outer housing 672. A cam member 682 is positioned within recess 678 and is maintained in contact with bump 676 by a urethane ring and washer assembly 682. Cam member 682 includes projections 685 which fit between inner ribs of outer housing 672. Cam member 682 has an end surface having a series of sloped surfaces 687 and shoulders 689 (FIG. 38C). In use, when opening 675 is slid over scalloped section 636 of housing 631 and outer housing 672 of torque wrench assembly 670 is gripped and rotated, cam member 682 is also rotated. The sloped surfaces 687 on cam member 682 slide over bump 676 until a respective shoulder engages bump 676, thereby rotating inner driver member 674 to consequently rotate transducer assembly 630. Inner driver 674 member will rotate with cam member 682 until the torque necessary to rotate transducer assembly 630 with respect to the vibration coupler (not shown) exceeds the force required to force the shoulders 689 over bump 676.

It will be understood that various modifications may be made to the embodiments herein. For example, vibration coupler 50 and blade 58 may be monolithically formed or attached using structure other than screw threads and the proximal end of ultrasonic transducer 630 need not have a scalloped configuration, but rather may be configured for engagement with any suitable torque wrench assembly. Further, the elongated body portion of the device need not be dimensioned to extend through a 5 mm trocar assembly, but rather may be dimensioned to extend through any size trocar assembly, e.g., 10 mm, 12 mm, etc. Therefore, the above description should not be construed as limiting, but merely as exemplifications of preferred embodiments. Those skilled in the art will envision other modifications within the scope and spirit of the claims appended hereto.

What is claimed is:

1. A surgical instrument for cutting body tissue comprising:
   a) a vibration coupler adapted to be operably connected to an ultrasonic generator and having a longitudinal axis;
   b) a blade member extending from a distal end portion of the vibration coupler, the blade member having a longitudinal axis generally aligned with the longitudinal axis of the vibration coupler and having a generally straight cutting surface forming an acute angle with respect to the longitudinal axis of the vibration coupler and forming an obtuse angle with respect to an axis perpendicular to a longitudinal axis of the vibration coupler; and
   c) a clamp member, the clamp member being movable from an open position spaced further from the cutting surface to a clamped position to capture tissue between the clamp and the cutting surface.

2. A surgical instrument according to claim 1, wherein the clamp member has a clamping surface, said clamping surface being parallel to the cutting surface when the clamp member is moved to the clamped position.

3. A surgical instrument according to claim 1, wherein the angle of the of the cutting surface with respect to the longitudinal axis of the vibration coupler is from about 30 degrees to about 70 degrees.

4. A surgical instrument according to claim 1, wherein the clamp member is moved linearly from the open position to the clamped position.

5. A surgical instrument according to claim 1, wherein the clamp member is pivoted from the open to the clamped position.

6. A surgical instrument according to claim 1, further including an actuation rod operably connected to the clamp member, the actuation rod being movable to move the clamp member from the open to the clamped position.

7. A surgical instrument according to claim 1, further comprising a biasing mechanism for biasing the clamp member to an open position with respect to the blade member.

8. A surgical instrument according to claim 1, wherein the cutting surface is planar.

9. A surgical instrument according to claim 1, wherein the cutting surface is linear.

10. A surgical instrument according to claim 1, wherein the blade member tapers in height towards its distal end.

11. An ultrasonic tissue dissector comprising:
   a) an elongated body portion;
   b) a vibration coupler adapted to be operably connected to an ultrasonic generator, the vibration coupler defining a longitudinal axis and positioned in the elongated body portion;
   c) a blade member extending from a distal end portion of the vibration coupler and a clamp member positioned adjacent the blade member, the blade member having a cutting surface disposed at a fixed acute angle to the longitudinal axis of the vibration coupler, the cutting surface extending downwardly and outwardly away from a central longitudinal axis of the elongated body portion and in a direction away from the clamp member in the distal direction and the clamp member having a tissue engaging surface movable between an open position spaced from the cutting surface of the blade member and a clamped position wherein the tissue engaging surface is moved toward the cutting surface.

12. An ultrasonic tissue dissector according to claim 11, further including an actuation rod operably connected to the clamp, the actuation rod being movable to move the clamp between the first and second positions.

13. An ultrasonic tissue dissector according to claim 12, wherein the clamp is moved linearly from the open to the clamped position.

14. An ultrasonic tissue dissector according to claim 12, wherein the clamp is pivoted from the open position to the clamped position.

15. An ultrasonic tissue dissector according to claim 12, further comprising a biasing mechanism for biasing the clamp member with respect to the blade member.

16. An ultrasonic tissue dissector according to claim 12, wherein the clamp is moved proximally into the clamped position.

17. An ultrasonic tissue dissector according to claim 11, wherein the cutting surface is planar.

18. A surgical instrument according to claim 11, wherein the cutting surface is linear.

19. A surgical instrument according to claim 11, further including a handle portion, the elongated body portion extending distally from the handle portion.

20. A surgical instrument according to claim 19, further including a transducer removably connected to the handle portion.

21. A surgical instrument according to claim 20, wherein the transducer includes an outer housing configured to engage a torque wrench.

22. A surgical instrument according to claim 20, wherein the transducer includes a transducer horn adapted to engage a proximal end of the vibration coupler.

23. A surgical instrument according to claim 22, wherein the transducer horn includes a threaded bore and the vibration coupler includes a threaded proximal end.

24. An ultrasonic system for dissecting tissue comprising:
   a) an ultrasonic generator;
   b) a housing;
   c) a vibration coupler operably connected to the ultrasonic generator, the vibration coupler positioned in the housing and defining a longitudinal axis and being adapted to vibrate in response to actuation of the ultrasonic generator;
   d) a blade member positioned adjacent a distal end portion of the vibration coupler, the blade member having a linear cutting surface forming an obtuse angle with respect to an axis perpendicular to the longitudinal axis of the housing and the longitudinal axis of the vibration coupler and being positioned to vibrate in response to vibration of the vibration coupler; and
   e) a clamp positioned adjacent the blade member, the clamp having a tissue engaging surface movable between an open position spaced from the planar cutting surface of the blade member and a clamped position wherein the tissue engaging surface is moved closer to the linear cutting surface of the blade member.

25. An ultrasonic system for dissecting tissue according to claim 24, wherein the clamp is moved linearly from the open to the clamped position.

26. An ultrasonic system for dissecting tissue according to claim 24, wherein the clamp is pivoted from the open position to the clamped position.

27. An ultrasonic system for dissecting tissue according to claim 24, wherein the clamp is moved proximally into the clamped position.

28. An ultrasonic dissector according to claim 24, wherein the blade member tapers in thickness toward the distal end.

29. An ultrasonic dissector according to claim 24, wherein the cutting surface is planar.

30. An ultrasonic instrument comprising:
   a) a vibration coupler adapted to be operably connected to an ultrasonic generator and having a longitudinal axis;
   b) a blade member extending from a distal end portion of the vibration coupler and having a longitudinal axis generally aligned with the longitudinal axis of the vibration coupler, the blade member having a linear cutting surface forming an acute angle $\Theta$ with respect to the longitudinal axis of the vibration coupler during vibration of the vibration coupler; and
   c) a clamp member having a tissue engaging surface, the clamp member being movable from an open position in which the tissue engaging surface is spaced from the cutting surface to a clamped position in which the clamp member is in juxtaposed alignment with the blade member to capture tissue between the tissue engaging surface and the cutting surface.

31. An ultrasonic instrument according to claim 30, wherein the tissue contact surface is parallel to the cutting surface when the clamp member is moved to the clamped position.

32. An ultrasonic instrument according to claim 31, wherein the tissue contact surface is removably fastened to the clamp member.

33. An ultrasonic instrument according to claim 30, wherein the angle $\Theta$ is from about 10 degrees to about 20 degrees.

34. An ultrasonic instrument according to claim 33, wherein the angle $\Theta$ is about 12 degrees.

35. An ultrasonic instrument according to claim 30, wherein the clamp member is pivoted from the open to the clamped position.

36. An ultrasonic instrument according to claim 30, further comprising a handle assembly and an actuator member operably connected to the handle assembly and to the clamp member, the handle assembly being movable to move the clamp member from the open position to the clamped position.

37. An ultrasonic instrument according to claim 36, wherein the clamp member includes a camming member positioned in a cam slot formed in the actuator member, the cam slot being movable relative to the camming member to pivot the clamp member between the open position and the clamped position.

38. An ultrasonic instrument according to claim 30, further comprising a rotatable collar operably associated with the vibration coupler, the clamp member, and the blade member such that rotation of the rotatable collar causes corresponding rotation of the vibration coupler, the clamp member and the blade member about the longitudinal axis of the vibration coupler.

39. An ultrasonic instrument according to claim 30, wherein the cutting surface is planar.

40. An ultrasonic instrument according to claim 30, wherein the vibration coupler, the blade member and, the clamp member are non-detachably connected and require no assembly prior to use.

41. An ultrasonic instrument according to claim 30, further including a handle portion, the vibration coupler extending distally from the handle portion.

42. An ultrasonic instrument according to claim 41, further including a transducer removably connected to the handle portion.

43. An ultrasonic instrument according to claim 42, wherein the transducer includes an outer housing configured to engage a torque wrench.

44. An ultrasonic instrument according to claim 42, wherein the transducer includes a transducer horn adapted to engage a proximal end of the vibration coupler.

45. An ultrasonic instrument according to claim 44, wherein the transducer horn includes a threaded bore and the vibration coupler includes a threaded proximal end configured to be received in the threaded bore.

46. An ultrasonic instrument comprising:
   a) a handle assembly; and
   b) an elongated body portion extending distally from the handle assembly, the elongated body portion including,
      1) an outer tubular member;
      2) a vibration coupler adapted to be operatively connected to an ultrasonic generator, the vibration coupler being positioned within the outer tubular member;
      3) a blade member operatively associated with the vibration coupler, the blade member having a planar cutting surface disposed at a fixed acute angle to the longitudinal axis of the vibration coupler; and
      4) a clamp member positioned adjacent the blade member, the clamp member having a tissue contact surface movable from an open position spaced from the cutting surface to a clamped position in juxtaposed alignment with the cutting surface to clamp tissue therebetween.

47. An ultrasonic instrument according to claim 46, wherein in the open position the clamp member and the blade member define a tissue receiving area, the clamp member having a tissue engaging member defining the proximal end of the tissue receiving area.

48. An ultrasonic instrument according to claim 47, wherein the handle assembly includes a handle movable between first and second positions, the movable handle being operatively associated with the clamp member to move the clamp member between the open and clamped positions as the movable handle is moved between the first and second positions.

49. An ultrasonic instrument according to claim 47, further comprising a tubular actuator member having a proximal end operatively connected to the movable handle and a distal end operatively connected to the clamp member.

50. An ultrasonic instrument according to claim 46, wherein the elongated body portion is dimensioned to be received within a 5 mm trocar assembly.

51. An ultrasonic instrument according to claim 46, wherein the blade member, the vibration coupler, and the clamp member are non-detachably connected and require no assembly prior to use.

52. An ultrasonic instrument according to claim 46, wherein the fixed acute angle is from about 10 to about 20 degrees.

53. An ultrasonic instrument according to claim 52, wherein the fixed acute angle is about 12 degrees.

54. An ultrasonic instrument according to claim 46, further including a transducer removably connected to the handle assembly.

55. An ultrasonic instrument according to claim 54, wherein the transducer includes an outer housing configured to be engaged by a torque wrench.

56. An ultrasonic instrument according to claim 54, wherein the transducer includes a transducer horn adapted to engage a proximal end of the vibration coupler.

57. An ultrasonic instrument according to claim 56, wherein the transducer horn includes a threaded bore and the vibration coupler includes a threaded proximal end.

58. An ultrasonic instrument according to claim 55, wherein the outer housing of the transducer is scallop-shaped.

59. An ultrasonic instrument according to claim 54, wherein the transducer includes an outer housing and a transducer horn positioned within the outer housing, the transducer further including at lest one O-ring positioned between the outer housing and the transducer horn.

60. An ultrasonic instrument according to claim 59, further including at least one spacer positioned between the outer housing and the transducer horn to urge the at least one O-ring longitudinally into the transducer horn.

* * * * *